(12) United States Patent
Shibuya

(10) Patent No.: US 7,169,529 B2
(45) Date of Patent: *Jan. 30, 2007

(54) COMPOUND, PHOTOSENSITIVE COMPOSITION, LITHOGRAPHIC PRINTING PLATE PRECURSOR, AND METHOD OF FORMING IMAGE

(75) Inventor: Akinori Shibuya, Shizuoka (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 90 days.

This patent is subject to a terminal disclaimer.

(21) Appl. No.: 10/838,316

(22) Filed: May 5, 2004

(65) Prior Publication Data

US 2004/0224257 A1    Nov. 11, 2004

(30) Foreign Application Priority Data

May 9, 2003    (JP)    ............... P.2003-131847

(51) Int. Cl.
G03F 7/004    (2006.01)
G03F 7/029    (2006.01)
C07D 293/00    (2006.01)

(52) U.S. Cl. .................. 430/270.1; 430/281.1; 430/311; 430/302; 548/100

(58) Field of Classification Search ............ 430/270.1, 430/311, 302, 281.1
See application file for complete search history.

(56) References Cited

U.S. PATENT DOCUMENTS 6,335,144 B1 *    1/2002    Murota et al. ........... 430/281.1

FOREIGN PATENT DOCUMENTS

| EP | 1 048 982 A1 | 11/2000 |
| EP | 1 091 247 A2 | 4/2001 |
| EP | 1 288 720 A1 | 3/2003 |
| EP | 1471387 A2 * | 10/2004 |
| EP | 1491536 A1 * | 12/2004 |
| JP | 2000-258910 A | 9/2000 |

OTHER PUBLICATIONS

English language machine translation of JP 2003-221517.*
European Search Report dated Nov. 17, 2004.

* cited by examiner

Primary Examiner—Amanda Walke
(74) Attorney, Agent, or Firm—Sughrue Mion, PLLC

(57) ABSTRACT

A compound having a novel structure and a photo-sensitive composition comprising (i) the novel compound as a sensitizing dye, (ii) an activator compound generating at least one of a radical and an acid by interacting the activator compound with light absorption of the sensitizing dye to cause chemical change, and (iii) a compound changing its physical or chemical property irreversibly by a reaction with at least one of the radical and the acid.

9 Claims, No Drawings

COMPOUND, PHOTOSENSITIVE COMPOSITION, LITHOGRAPHIC PRINTING PLATE PRECURSOR, AND METHOD OF FORMING IMAGE

BACKGROUND OF THE INVENTION

1. Field of the Invention

The present invention relates to a novel sensitizing dye and a photoinitiation system using the sensitizing dye. More specifically, the present invention relates to a photosensitive composition containing a photoinitiation system having high sensitivity and excellent stability. The present invention also relates to a photopolymerizable composition excellent as a material for a lithographic printing plate precursor capable of producing a printing plate by scanning exposure based on digital signals.

2. Description of the Related Art

In the related art, a PS plate having a construction such that a lipophilic photosensitive resin layer is provided on a hydrophilic support has been widely used as a lithographic printing plate, and a desired printing plate has been generally obtained by a plate-making method where masking exposure (surface exposure) is performed via a lith film and then the non-image area is dissolved and removed.

In recent years, digitization techniques of electronically processing, storing and outputting image information by using a computer have been widespread and various corresponding new image output systems have been put into practical use. As a result, there arises a demand for a computer-to-plate (CTP) technique of directly producing a printing plate without using a lith film, by scanning high directivity light such as laser light based on digitized image information, and production of a printing plate precursor suited for such a technique is now an important technical subject.

As one of the methods for obtaining such a lithographic printing plate by scanning exposure, a construction such that a photopolymerization system composition having excellent sensitization speed is used for the ink-accepting photosensitive resin layer (hereinafter referred to as a "photosensitive layer") provided on a hydrophilic support has been heretofore proposed and this is already available on the market. The printing plate precursor having such a construction is facilitated in the development processing and favored with good plate-making and printing performances of giving excellent resolution, inking property, press life and scumming resistance.

The above-described photopolymerizable composition basically comprises an ethylenic unsaturated compound, a photopolymerization initiation system and a binder resin, where the photoinitiation system absorbs light to produce an active radical and this radical induces the addition polymerization of the ethylenic unsaturated compound to cause insolubilization of the photosensitive layer, as a result, an image is formed.

Most of the related-art proposals regarding the photopolymerizable composition capable of being scan-exposed use a photoinitiation system having excellent photosensitivity and many compositions are described, for example, in Bruce M. Monroe et al., *Chemical Review*, Vol. 93, pp. 435–448 (1993) and R. S. Davidson, *Journal of Photochemistry and Biology A: Chemistry*, Vol. 73, pp. 81–96 (1993).

With respect to the related-art CTP systems where a photopolymerizable composition comprising such an initiation system is used and a long wavelength visible light source such as Ar laser (488 nm) or FD-YAG laser (532 nm) is used as the light source, writing at a higher speed is demanded for the purpose of improving productivity in the plate-making step, but this has not yet been achieved because of insufficient output of the light source and insufficient sensitivity of the photosensitive material.

On the other hand, a semiconductor laser which uses, for example, an InGaN-base material and can effect continuous oscillation in the region from 350 to 450 nm has been recently put into practical use. The scanning exposure system using such a short-wave light source is advantageous in that the semiconductor laser can be produced at a low cost in view of its structure and therefore, an economical system having sufficiently high output can be constructed. In addition, as compared with the related-art systems using an FD-YAG or Ar laser, a photosensitive material having photosensitivity in the short-wave region and capable of being worked under brighter safe light can be used.

However, a photoinitiation system having sufficiently high sensitivity for scanning exposure in the short-wavelength region from 350 to 450 nm is not yet known at present.

Furthermore, the technique for obtaining a photoinitiation system having high sensitivity is still keenly demanded in the imaging field (see, for example, JP-A-2000-258910 (the term "JP-A" as used herein means an "unexamined published Japanese patent application"), J. P. Faussier, *Photoinitiated Polymerization-Theory and Applications: Rapra Review*, Vol. 9, Report, Rapra Technology (1998), and M. Tsunooka et al., *Prog. Polym. Sci.*, 21, 1 (1996)). The photoinitiation system comprising a sensitizing dye and an activator can generate an acid or a base other than the above-described radical by selecting the activator and therefore, this system is used, for example, in the image formation such as stereolithography, holography and color hard copy, in the production field of electronic materials such as photoresist, and in uses as a photocurable resin material for ink, coating material, adhesive or the like. In these industrial fields, in order to cause decomposition of the activator with good efficiency, it is demanded to find out a sensitizing dye having excellent light absorption and sensitization ability.

SUMMARY OF THE INVENTION

An object of the present invention is to provide a photosensitive composition having high sensitivity to the wavelength over a wide range from 350 to 450 nm, high press life and good compatibility and being suited for a lithographic printing plate precursor or the like highly sensitive to the oscillation wavelength of a short-wave semiconductor laser and thereby obtain a lithographic printing plate or the like for scanning exposure, which is ensured with excellent workability, high profitability and good suitability for CTP system.

As a result of intensive investigations to attain the above-described object, the present inventors have found that a novel photoinitiation system comprising a novel sensitizing dye having a specific structure and an activator as the polymerization initiator gives particularly high sensitivity. The present invention has been accomplished based on this finding.

That is, the present invention provides the followings.

(1) A compound represented by formula (1):

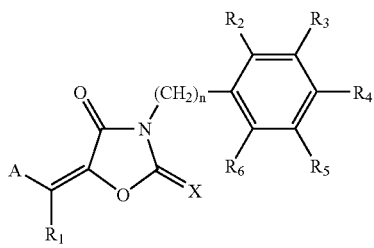

(1)

wherein A represents an aromatic or heterocyclic ring which may have a substituent; X represents an oxygen atom, a sulfur atom or $=NR_7$; $R_1$, $R_2$, $R_3$, $R_4$, $R_5$, $R_6$ and $R_7$ each independently represents a hydrogen atom or a monovalent nonmetallic atom group, provided that at least one of $R_2$, $R_3$, $R_4$, $R_5$ and $R_6$ is a substituent represented by $-OR_8$, in which $R_8$ independently represents a monovalent nonmetallic atom group; and n represents an integer of 1 to 6.

(2) The compound described in (1), which is represented by formula (2):

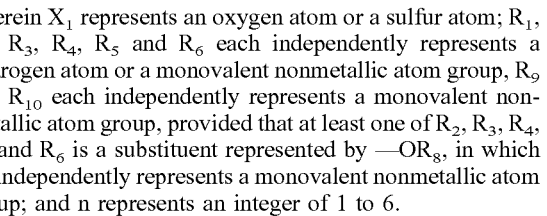

(2)

wherein $X_1$ represents an oxygen atom or a sulfur atom; $R_1$, $R_2$, $R_3$, $R_4$, $R_5$ and $R_6$ each independently represents a hydrogen atom or a monovalent nonmetallic atom group, $R_9$ and $R_{10}$ each independently represents a monovalent nonmetallic atom group, provided that at least one of $R_2$, $R_3$, $R_4$, $R_5$ and $R_6$ is a substituent represented by $-OR_8$, in which $R_8$ independently represents a monovalent nonmetallic atom group; and n represents an integer of 1 to 6.

(3) A photosensitive composition comprising:

(i) a sensitizing dye represented by formula (1);

(ii) an activator compound generating at least one of a radical and an acid by interacting the activator compound with light absorption of the sensitizing dye represented by formula (1) to cause chemical change; and (iii) a compound changing its physical or chemical property irreversibly by a reaction with at least one of the radical and the acid:

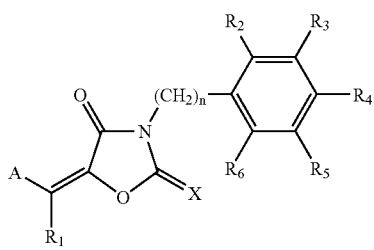

(1)

wherein A represents an aromatic or heterocyclic ring which may have a substituent; X represents an oxygen atom, a sulfur atom or $=NR_7$; $R_1$, $R_2$, $R_3$, $R_4$, $R_5$, $R_6$ and $R_7$ each independently represents a hydrogen atom or a monovalent nonmetallic atom group, provided that at least one of $R_2$, $R_3$, $R_4$, $R_5$ and $R_6$ is a substituent represented by $-OR_8$, in which $R_8$ independently represents a monovalent nonmetallic atom group; and n represents an integer of 1 to 6.

(4) The photosensitive composition described in (3), wherein the sensitizing dye (i) is represented by formula (2):

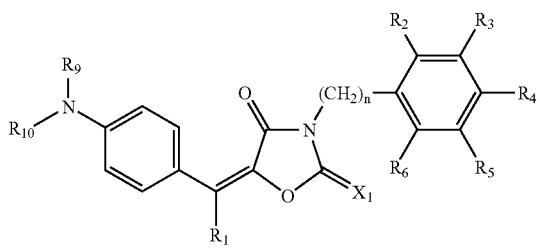

(2)

wherein $X_1$ represents an oxygen atom or a sulfur atom; $R_1$, $R_2$, $R_3$, $R_4$, $R_5$ and $R_6$ each independently represents a hydrogen atom or a monovalent nonmetallic atom group, $R_9$ and $R_{10}$ each independently represents a monovalent nonmetallic atom group, provided that at least one of $R_2$, $R_3$, $R_4$, $R_5$ and $R_6$ is a substituent represented by $-OR_8$, in which $R_8$ independently represents a monovalent nonmetallic atom group; and n represents an integer of 1 to 6.

(5) The photosensitive composition described in (3) or (4), wherein the compound (iii) is an addition-polymerizable compound having an ethylenic unsaturated double bond.

(6) A lithographic printing plate precursor comprising: a photosensitive layer including the photosensitive composition described in any of (3) to (5).

(7) A method of forming image comprising: exposing a predetermined area of a photosensitive layer including the photosensitive composition described in any of (3) to (5).

(8) The method described in (7), further comprising: developing one of the predetermined area and the other area.

The compound represented by formula (1) of the present invention is a novel compound.

The lithographic printing plate precursor using a photosensitive composition containing, as a sensitizing dye, the compound represented by formula (1) of the present invention gives a lithographic printing plate having sufficiently high sensitivity for scanning exposure by a laser light source at a wavelength shorter than 450 nm, which can be handled even under bright safe light and exhibits excellent press life and scumming resistance.

DETAILED DESCRIPTION OF THE INVENTION

The embodiment of the present invention is described in detail below.

A. Photoinitiation System

The photoinitiation system of the present invention comprises (i) a novel sensitizing dye having a specific structure represented by formula (1) and (ii) an activator compound generating at least one of a radical and an acid by interacting the activator compound with light absorption of the sensitizing dye to cause chemical change.

One of the characteristic features of the sensitizing dye (i) of the present invention is to have excellent absorption property particularly in the region from 350 to 450 nm. In addition, the dye (i) brings about decomposition of various activators with good efficiency to show very high photosensitivity. Generally, the sensitization mechanism of a photo-initiation system comprising a sensitizing dye/an activator is known to have routes such as (1) reductive decomposition of the activator, based on the electron transfer from the electronic excitation state of the sensitizing dye to the activator, (2) oxidative decomposition of the activator, based on the electron transfer from the activator to the electronic excitation state of the sensitizing dye and (3) decomposition of the activator from its electronic excitation state, based on the energy transfer from the electronic excitation state of the sensitizing dye to the activator. The sensitizing dye of the present invention has been found to bring about any type of these sensitization reactions with excellent efficiency.

The present inventors have found that the novel compound represented by formula (1) shows high sensitivity as the sensitizing dye. The reason why the specific structure represented by formula (1) is very important for the elevation of sensitivity is not clear known, but since the sensitizing dye shows a high-intensity emission (fluorescence and/or phosphorescence) spectrum, it is considered as one of possibilities that the sensitizing dye of the present invention has a relatively long excitation life and this contributes to the efficiency of reaction with the activator. Furthermore, it has been found that by having a substituent such as alkoxy group, aryloxy group or oxycarbonyl group, the sensitizing dye of the present invention is prevented from crystallization during storage, that is, remarkably enhanced in the storage stability. The reason therefor is not clearly known, but the presence of a substituent having high polarity is considered to increase the compatibility in the photosensitive composition layer and thereby contribute to the enhanced storage stability.

(A1) Sensitizing Dye

The sensitizing dye for use in the present invention is a compound represented by the following formula (1):

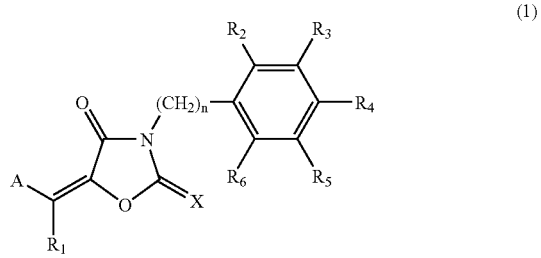

(1)

(wherein A represents an aromatic or heterocyclic ring which may have a substituent, X represents an oxygen atom, a sulfur atom or =$NR_7$, $R_1$, $R_2$, $R_3$, $R_4$, $R_5$, $R_6$ and $R_7$ each independently represents a hydrogen atom or a monovalent nonmetallic atom group, provided that at least one of $R_2$, $R_3$, $R_4$, $R_5$ and $R_6$ is a substituent represented by —$OR_8$ (wherein $R_8$ independently represents a monovalent nonmetallic atom group), and n represents an integer of 1 to 6).

Formula (1) is described in detail below.

The monovalent nonmetallic atom group represented by $R_1$, $R_2$, $R_3$, $R_4$, $R_5$, $R_6$, $R_7$ and $R_8$ (hereinafter sometimes simply referred to as "$R_1$ to $R_8$") is preferably a substituted or unsubstituted alkyl group, a substituted or unsubstituted alkenyl group, a substituted or unsubstituted aryl group, a substituted or unsubstituted aromatic heterocyclic group, a substituted or unsubstituted alkynyl group, a substituted or unsubstituted alkoxy group, a substituted or unsubstituted alkylthio group, a hydroxyl group, an acyl group or a halogen atom.

Preferred examples of $R_1$ to $R_8$ are specifically described below.

Preferred examples of the alkyl group include a linear, branched or cyclic alkyl group having from 1 to 20 carbon atoms, and specific examples thereof include a methyl group, an ethyl group, a propyl group, a butyl group, a pentyl group, a hexyl group, a heptyl group, an octyl group, a nonyl group, a decyl group, an undecyl group, a dodecyl group, a tridecyl group, a hexadecyl group, an octadecyl group, an eicosyl group, an isopropyl group, an isobutyl group, a s-butyl group, a tert-butyl group, an isopentyl group, a neopentyl group, a 1-methylbutyl group, an isohexyl group, a 2-ethylhexyl group, a 2-methylhexyl group, a cyclohexyl group, a cyclopentyl group and a 2-norbornyl group. Among these, preferred are a linear alkyl group having from 1 to 12 carbon atoms, a branched alkyl group having from 3 to 12 carbon atoms and a cyclic alkyl group having from 5 to 10 carbon atoms.

As the substituent of the substituted alkyl group, a monovalent nonmetallic atom group excluding hydrogen is used, and preferred examples thereof include a halogen atom (e.g., —F, —Br, —Cl, —I), a hydroxyl group, an alkoxy group, an aryloxy group, a mercapto group, an alkylthio group, an arylthio group, an alkyldithio group, an aryldithio group, an amino group, an N-alkylamino group, an N,N-dialkylamino group, an N-arylamino group, an N,N-diarylamino group, an N-alkyl-N-arylamino group, an acyloxy group, a carbamoyloxy group, an N-alkylcarbamoyloxy group, an N-arylcarbamoyloxy group, an N,N-dialkylcarbamoyloxy group, an N,N-diarylcarbamoyloxy group, an N-alkyl-N-arylcarbamoyloxy group, an alkylsulfoxy group, an arylsulfoxy group, an acylthio group, an acylamino group, an N-alkylacylamino group, an N-arylacylamino group, a ureido group, an N'-alkylureido group, an N',N'-dialkylureido group, an N'-arylureido group, an N',N'-diarylureido group, an N'-alkyl-N'-arylureido group, an N-alkylureido group, an N-arylureido group, an N'-alkyl-N-alkylureido group, an N'-alkyl-N-arylureido group, an N',N'-dialkyl-N-alkylureido group, an N',N'-dialkyl-N-arylureido group, an N'-aryl-N-alkylureido group, an N'-aryl-N-arylureido group, an N',N'-diaryl-N-alkylureido group, an N',N'-diaryl-N-arylureido group, an N'-alkyl-N'-aryl-N-alkylureido group, an N'-alkyl-N'-aryl-N-arylureido group, an alkoxycarbonylamino group, an aryloxycarbonylamino group, an N-alkyl-N-alkoxycarbonylamino group, an N-alkyl-N-aryloxycarbonyl-amino group, an N-aryl-N-alkoxycarbonylamino group, an N-aryl-N-aryloxycarbonylamino group, a formyl group, an acyl group, a carboxyl group, an alkoxycarbonyl group, an aryloxycarbonyl group, carbamoyl group, an N-alkylcarbamoyl group, an N,N-dialkylcarbamoyl group, an N-arylcarbamoyl group, an N,N-diarylcarbamoyl group, an N-alkyl-N-arylcarbamoyl group, an alkylsulfinyl group, an arylsulfinyl group, an alkylsulfonyl group, an arylsulfonyl group, a sulfo group (—$SO_3H$) and its conjugate base group (hereinafter referred to as a sulfonato group), an alkoxysulfonyl group, an aryloxysulfonyl group, a sulfinamoyl group, an N-alkylsulfinamoyl group, an N,N-dialkylsulfinamoyl group, an N-arylsulfinamoyl group, an N,N-diarylsulfinamoyl group, an N-alkyl-N-arylsulfinamoyl group, a sulfamoyl group, an N-alkylsulfamoyl group, an N,N-dialkylsulfamoyl group, an N-arylsulfamoyl group, an N,N-diarylsulfamoyl group, an N-alkyl-N-arylsulfamoyl group, a phosphono group ($-PO_3H_2$) and its conjugate base group (hereinafter referred to as a phosphonato group), a dialkylphosphono group ($-PO_3(alkyl)_2$), a diarylphosphono group ($-PO_3(aryl)_2$) an alkylarylphosphono group ($-PO_3(alkyl)(aryl)$), a monoalkylphosphono group ($-PO_3H(alkyl)$) and its conjugate base group (hereinafter referred to as an alkylphosphonato group), a monoaryl-phosphono group ($-PO_3H(aryl)$) and its conjugate base group (hereinafter referred to as an arylphosphonato group), a phosphonooxy group ($-OPO_3H_2$) and its conjugate base group (hereinafter referred to as a phosphonatooxy group), a dialkylphosphonooxy group ($-OPO_3(alkyl)_2$), a diaryl-phosphonooxy group ($-OPO_3(aryl)_2$), an alkylarylphosphonooxy group ($-OPO_3(alkyl)(aryl)$), a monoalkylphosphonooxy group ($-OPO_3H(alkyl)$) and its conjugate base group (hereinafter referred to as an alkylphosphonatooxy group), a monoarylphosphonooxy group ($-OPO_3H(aryl)$) and its conjugate base group (hereinafter referred to as an arylphosphonatooxy group), a cyano group, a nitro group, an aryl group, a heteroaryl group, an alkenyl group and an alkynyl group.

Specific examples of the alkyl group in these substituents include the alkyl groups described above, and specific examples of the aryl group include a phenyl group, a biphenyl group, a naphthyl group, a tolyl group, a xylyl group, a mesityl group, a cumenyl group, a chlorophenyl group, a bromophenyl group, a chloromethylphenyl group, a hydroxyphenyl group, a methoxyphenyl group, an ethoxyphenyl group, a phenoxyphenyl group, an acetoxyphenyl group, a benzoyloxyphenyl group, a methylthiophenyl group, a phenylthiophenyl group, a methylaminophenyl group, a dimethylaminophenyl group, an acetylaminophenyl group, a carboxyphenyl group, a methoxycarbonylphenyl group, an ethoxyphenylcarbonyl group, a phenoxycarbonylphenyl group, an N-phenylcarbamoylphenyl group, a phenyl group, a cyanophenyl group, a sulfophenyl group, a sulfonatophenyl group, a phosphonophenyl group and a phosphonatophenyl group.

As the aromatic heterocyclic group represented by $R_1$ to $R_8$, a monocyclic or polycyclic aromatic ring containing at least one of a nitrogen atom, an oxygen atom and a sulfur atom is used, and particularly preferred examples of the aromatic heterocyclic group include thiophene, thiathrene, furan, pyran, isobenzofuran, chromene, xanthene, phenoxazine, pyrrole, pyrazole, isothiazole, isoxazole, pyrazine, pyrimidine, pyridazine, indolizine, isoindolizine, indolyl, indazole, purine, quinolizine, isoquinoline, phthalazine, naphthyridine, quinazoline, cinnoline, pteridine, carbazole, carboline, phenanthrene, acridine, perimidine, phenanthroline, phthalazine, phenarsazine, phenoxazine, furazane and phenoxazine. These groups each may be further condensed with a benzo ring or may have a substituent.

Preferred examples of the alkenyl group represented by $R_1$ to $R_8$ include a vinyl group, a 1-propenyl group, albutenyl group, a cinnamyl group and a 2-chloro-1-ethenyl group, and preferred examples of the alkynyl group include an ethynyl group, a 1-propynyl group, a 1-butynyl group and a trimethylsilylethynyl group. Examples of G1 in the acyl group (G1CO—) include hydrogen and the above-described alkyl and aryl groups.

Among these substituents, more preferred are a halogen atom (e.g., —F, —Br, —Cl, —I), an alkoxy group, an aryloxy group, an alkylthio group, an arylthio group, an N-alkylamino group, an N,N-dialkylamino group, an acyloxy group, an N-alkylcarbamoyloxy group, an N-arylcarbamoyloxy group, an acylamino group, a formyl group, an acyl group, a carboxyl group, an alkoxycarbonyl group, an aryloxycarbonyl group, a carbamoyl group, an N-alkylcarbamoyl group, an N,N-dialkylcarbamoyl group, an N-arylcarbamoyl group, an N-alkyl-N-arylcarbamoyl group, a sulfo group, a sulfonato group, a sulfamoyl group, an N-alkylsulfamoyl group, an N,N-dialkylsulfamoyl group, an N-arylsulfamoyl group, an N-alkyl-N-arylsulfamoyl group, a phosphono group, a phosphonato group, a dialkylphosphono group, a diarylphosphono group, a monoalkylphosphono group, an alkylphosphonato group, a monoarylphosphono group, an arylphosphonato group, a phosphonooxy group, a phosphonatooxy group, an aryl group and an alkenyl group.

The alkylene group in the substituted alkyl group includes a divalent organic residue resulting from removing any one of hydrogen atoms on the above-described alkyl group having from 1 to 20 carbon atoms, and preferred examples thereof include a linear alkylene group having from 1 to 12 carbon atoms, a branched alkylene group having from 3 to 12 carbon atoms and a cyclic alkylene group having from 5 to 10 carbon atoms.

Specific examples of the substituted alkyl group preferred as $R_1$ to $R_8$, which is obtained by combining the above-described substituent and an alkylene group, include a chloromethyl group, a bromomethyl group, a 2-chloroethyl group, a trifluoromethyl group, a methoxymethyl group, a methoxyethoxyethyl group, an allyloxymethyl group, a phenoxymethyl group, a methylthiomethyl group, a tolylthiomethyl group, an ethylaminoethyl group, a diethylaminopropyl group, a morpholinopropyl group, an acetyloxymethyl group, a benzoyloxymethyl group, an N-cyclohexylcarbamoyloxyethyl group, an N-phenylcarbamoyloxyethyl group, an acetylaminoethyl group, an N-methylbenzoylaminopropyl group, a 2-oxoethyl group, a 2-oxopropyl group, a carboxypropyl group, a methoxycarbonylethyl group, an allyloxycarbonylbutyl group, a chlorophenoxycarbonylmethyl group, a carbamoylmethyl group, an N-methylcarbamoylethyl group, an N,N-dipropylcarbamoylmethyl group, an N-(methoxyphenyl)carbamoylethyl group, an N-methyl-N-(sulfophenyl)carbamoylmethyl group, a sulfobutyl group, a sulfonatobutyl group, a sulfamoylbutyl group, a N-ethylsulfamoylmethyl group, an N,N-dipropylsulfamoylpropyl group, an N-tolylsulfamoylpropyl group, an N-methyl-N-(phosphonophenyl)sulfamoyloctyl group, a phosphonobutyl group, a phosphonatohexyl group, a diethylphosphonobutyl group, a diphenylphosphonopropyl group, a methylphosphonobutyl group, a methylphosphonatobutyl group, a tolylphosphonohexyl group, a tolylphosphonatohexyl group, a phosohonooxypropyl group, a phosphonatooxybutyl group, a benzyl group, a phenethyl group, an α-methylbenzyl group, a 1-methyl-1-phenylethyl group, a p-methylbenzyl group, a cinnamyl group, an allyl group, a 1-propenylmethyl group, a 2-butenyl group, a 2-methylallyl group, a 2-methylpropenylmethyl group, a 2-propynyl group, a 2-butynyl group and 3-butynyl group.

The aryl group preferred as $R_1$ to $R_8$ specifically includes a condensed ring formed by 1 to 3 benzene rings, and a condensed ring formed by a benzene ring and a 5-membered unsaturated ring, and specific examples thereof include a phenyl group, a naphthyl group, an anthryl group, a phenanthryl group, an indenyl group, an acenaphthenyl group and a fluorenyl group. Among these, a phenyl group and a naphthyl group are more preferred.

The substituted aryl group preferred as $R_1$ to $R_8$ specifically includes a substituted aryl group where a monovalent nonmetallic atom group excluding hydrogen is present as a substituent on the ring-forming carbon atom of the above-described aryl group. Preferred examples of the substituent include the above-described alkyl groups and substituted alkyl groups and those described above as the substituent in the substituted alkyl group. Preferred specific examples of the substituted aryl group include a biphenyl group, a tolyl group, a xylyl group, a mesityl group, a cumenyl group, a chlorophenyl group, a bromophenyl group, a fluorophenyl group, a chloromethylphenyl group, a trifluoromethylphenyl group, a hydroxyphenyl group, a methoxyphenyl group, a methoxyethoxyphenyl group, an allyl-oxyphenyl group, a phenoxyphenyl group, a methylthiophenyl group, a tolylthiophenyl group, an ethylaminophenyl group, a diethylaminophenyl group, a morpholinophenyl group, an acetyloxyphenyl group, a benzoyloxyphenyl group, an N-cyclohexylcarbamoyloxyphenyl group, an N-phenylcarbamoyloxyphenyl group, an acetylaminophenyl group, an N-methylbenzoylaminophenyl group, a carboxyphenyl group, a methoxycarbonylphenyl group, an allyloxycarbonylphenyl group, a chlorophenoxycarbonylphenyl group, a carbamoylphenyl group, an N-methylcarbamoylphenyl group, an N,N-dipropylcarbamoylphenyl group, an N-(methoxyphenyl)carbamoylphenyl group, an N-methyl-N-(sulfophenyl)carbamoylphenyl group, a sulfophenyl group, a sulfonatophenyl group, a sulfamoylphenyl group, an N-ethylsulfamoylphenyl group, an N,N-dipropylsulfamoylphenyl group, an N-tolylsulfamoylphenyl group, an N-methyl-N-(phosphonophenyl)sulfamoylphenyl group, a phosphonophenyl group, a phosphanatophenyl group, a diethylphosphonophenyl group, a diphenylphosphonophenyl group, a methylphosphonophenyl group, a methylphosphonatophenyl group, a tolylphosphonophenyl group, a tolylphosphonatophenyl group, an allyl group, a 1-propenylmethyl group, a 2-butenyl group, a 2-methylallylphenyl group, a 2-methylpropenylphenyl group, a 2-propynylphenyl group, a 2-butynylphenyl group and 3-butynylphenyl group.

$R_2$, $R_3$, $R_4$, $R_5$ and $R_6$ each is more preferably a hydrogen atom or a substituted or unsubstituted alkyl group. $R_8$ is more preferably a substituted or unsubstituted alkyl group, still more preferably an ethyl group or a methyl group.

n is preferably an integer of 2 to 5, more preferably 2 or 3.

A in formula (1) is described below. A represents an aromatic or heterocyclic ring which may have a substituent. Specific examples of the aromatic or heterocyclic ring which may have a substituent include those described above for $R_1$ to $R_8$ in formula (1).

Among these sensitizing dyes represented by formula (1), a sensitizing dye represented by the following formula (2) is preferred, because this sensitizing dye has high sensitization ability and gives a photosensitive composition having excellent storage stability:

(2)

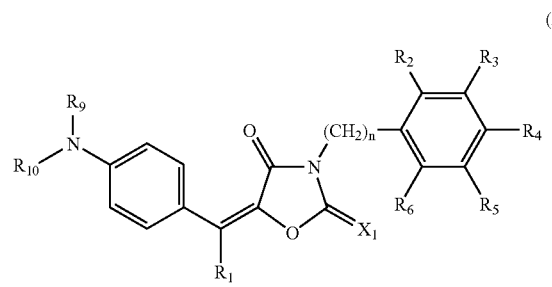

(wherein $X_1$ represents an oxygen atom or a sulfur atom, $R_1$, $R_2$, $R_3$, $R_4$, $R_5$ and $R_6$ each independently represents a hydrogen atom or a monovalent nonmetallic atom group, $R_9$ and $R_{10}$ each independently represents a monovalent nonmetallic atom group, provided that at least one of $R_2$, $R_3$, $R_4$, $R_5$ and $R_6$ is a substituent represented by —$OR_8$ (wherein $R_8$ independently represents a monovalent nonmetallic atom group), and n represents an integer of 1 to 6).

In formula (2), $R_1$, $R_2$, $R_3$, $R_4$, $R_5$, $R_6$ and $R_8$ have the same meanings as in formula (2). $R_9$ and $R_{10}$ each independently represents a monovalent nonmetallic atom group and preferred specific examples include the groups described above for $R_2$, $R_3$, $R_4$, $R_5$ and $R_6$. More preferred examples of $R_9$ and $R_{10}$ include an aryl or heterocyclic group which may have a substituent.

The sensitizing dyes represented by formulae of the present invention can be obtained by the condensation reaction of the above-described acidic nucleus or an acidic nucleus having an active methylene group with a substituted or unsubstituted aromatic or heterocyclic ring and these can be synthesized by referring to JP-B-59-28329 (the term "JP-B" as used herein means an "examined Japanese patent publication").

Preferred specific examples ((D1) to (D32)) of the compound represented by formula (1) are set forth below, however, the present invention is not limited thereto. Also, isomers with respect to the double bond connecting an acidic nucleus and a basic nucleus are not clear and the present invention is not limited to either one isomer.

(D1)

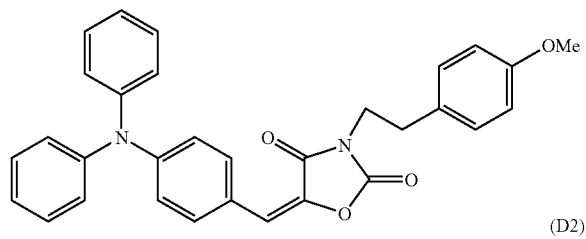

(D2)

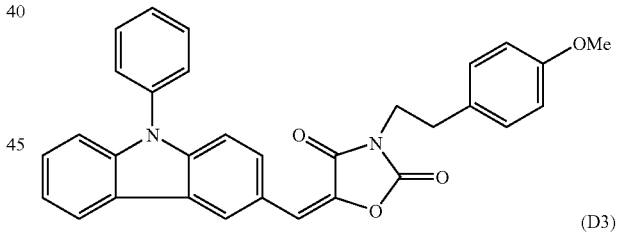

(D3)

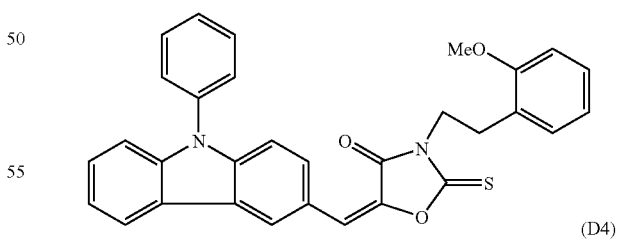

(D4)

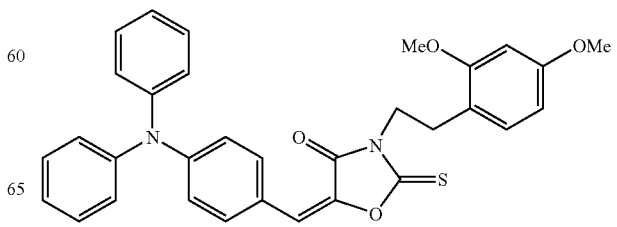

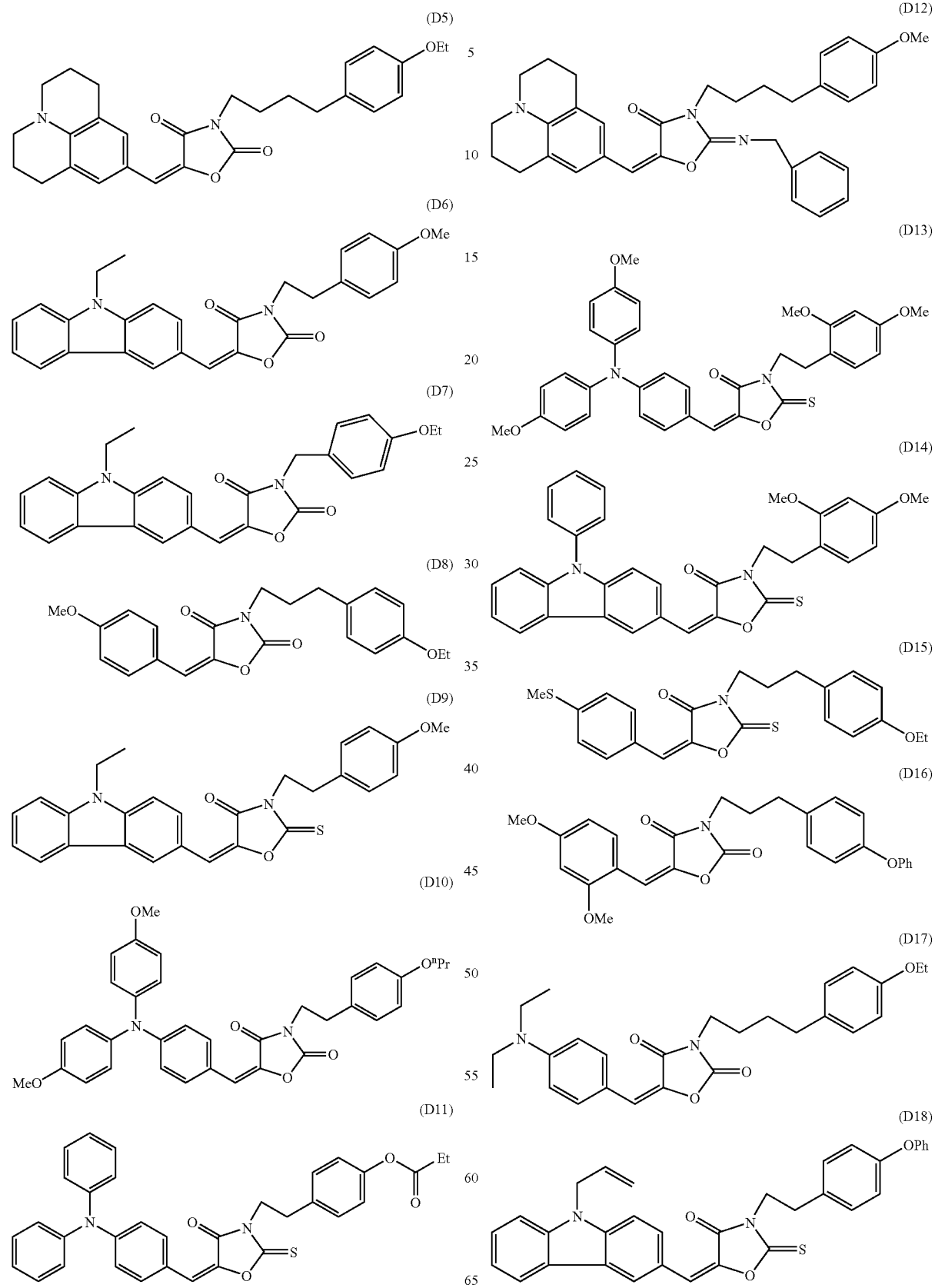

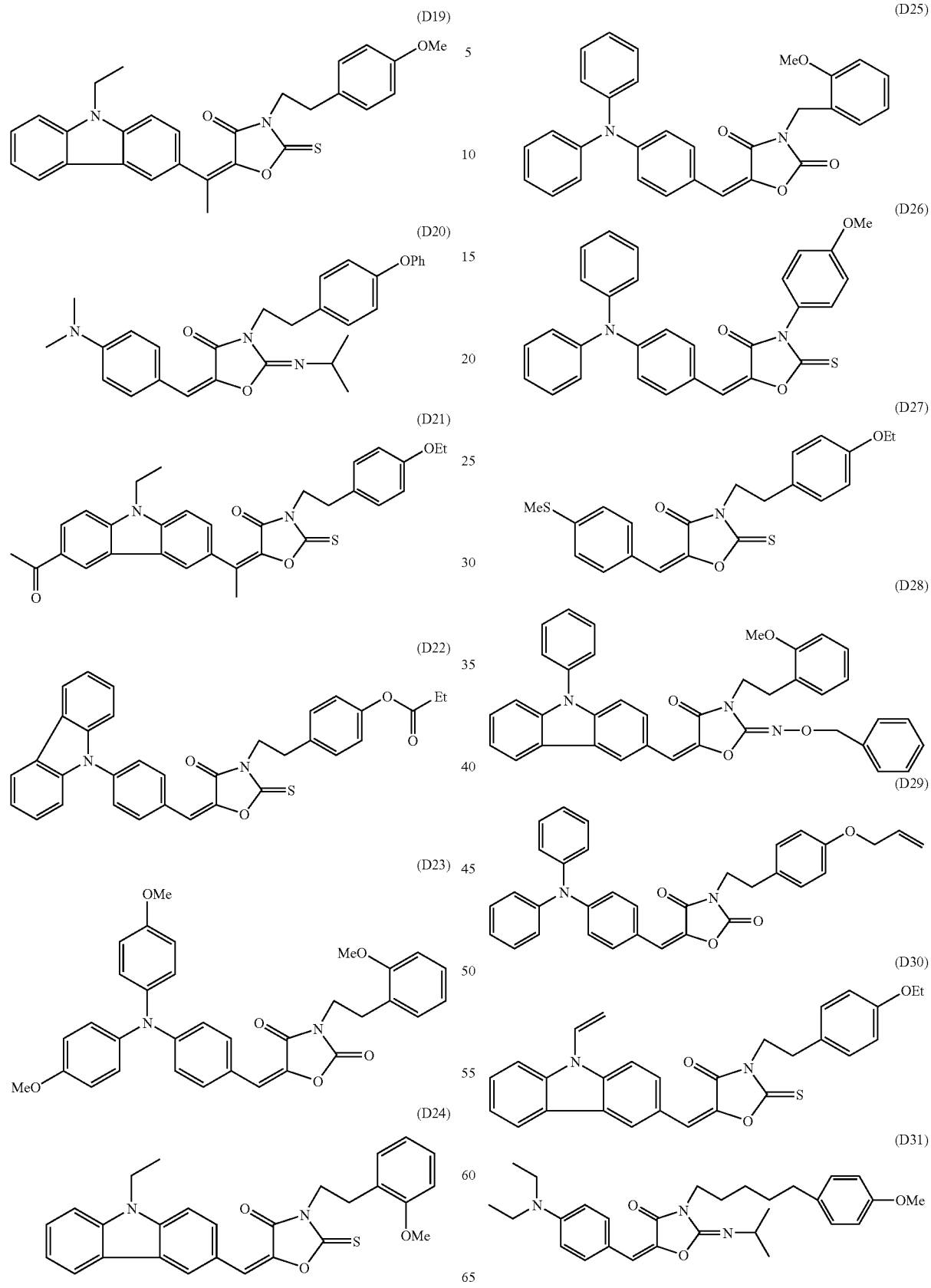

-continued (D32)

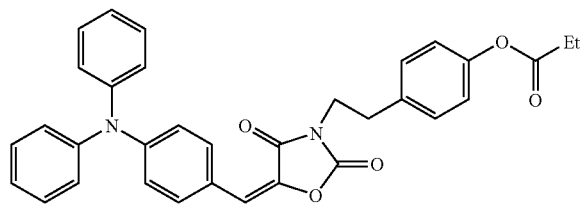

The sensitizing dye of the present invention may be subjected to various chemical modifications so as to improve the properties of the photosensitive layer. For example, the sensitizing dye may be bound with an addition-polymerizable compound structure (e.g., acryloyl group, methacryloyl group) by covalent bonding, ionic bonding, hydrogen bonding or the like, whereby the strength of exposure film can be increased or unnecessary precipitation of the dye from the film after exposure can be inhibited. Also, the sensitizing dye may be bound with the part of generating a radical, an acid or a base of an activator compound which is described later, whereby photosensitivity particularly in a low concentration state of the initiation system can be remarkably increased. For the purpose of enhancing the processing aptitude for an (alkali) aqueous developer, which is a preferred use mode of the photosensitive layer of the present invention, introduction of a hydrophilic moiety (an acidic group or a polar group, such as carboxyl group or its ester, sulfonic group or its ester, and ethylene oxide group) is effective. Particularly, an ester-type hydrophilic group has property such that it forms a relatively hydrophobic structure in the photosensitive layer to afford excellent compatibility and produces an acid radical due to hydrolysis in the developer to increase the hydrophilic property. Other than these, a substituent may be appropriately introduced so as to, for example, improve compatibility and inhibit crystallization in the photosensitive layer. For example, in a certain photosensitive system, an unsaturated bond of an aryl group, an allyl group or the like is sometimes very effective in improving the compatibility, or crystallization can be significantly inhibited when steric hindrance between dye π planes is introduced by a method such as introduction of a branched alkyl structure. Also, the adhesion to an inorganic material such as metal or metal oxide can be enhanced by introducing a phosphonic group, an epoxy group, a trialkoxysilyl group or the like. In addition, if desired, formation of the sensitizing dye into a polymer may also be used.

On use of the sensitizing dye, details such as structure selected, single use or combination use of two or more, and amount added, can be appropriately set according to the performance design of the final photosensitive material. For example, the compatibility in the photosensitive layer can be increased by using two or more sensitizing dyes in combination. In the selection of the sensitizing dye, the molar absorption coefficient at the emission wavelength of the light source used is an important factor. When a dye having a large molar absorption coefficient is used, the amount of the dye added can be relatively small and this is profitable and also advantageous in view of physical properties of the photosensitive layer. The photosensitivity and resolution of the photosensitive layer and the physical properties of the exposure film are largely affected by the absorbance at the light source wavelength and therefore, the amount of the sensitizing dye added is appropriately selected by taking account of these factors. For example, when the absorbance is in a low region of 0.1 or less, the sensitivity decreases and also, low resolution results due to halation. However, for the purpose of hardening a film having, for example, a thickness of 5 μm or more, such a low absorbance is sometimes rather effective in increasing the hardening degree. In addition, when the absorbance is in a high region of 3 or more, the light is mostly absorbed on the surface of the photosensitive layer and hardening in more inner part is inhibited, as a result, in use, for example, as a printing plate, the printing plate is insufficient in the film strength and adhesion to substrate. In the case of a lithographic printing plate where the layer is used in a relatively small thickness, the amount of the sensitizing dye added is preferably set to give a photosensitive layer having an absorbance of 0.1 to 1.5, preferably from 0.25 to 1. In use as a lithographic printing plate, the amount added is generally from 0.05 to 30 parts by mass, preferably from 0.1 to 20 parts by mass, more preferably from 0.2 to 10 parts by mass, per 100 parts by mass of the photosensitive layer components.

(A2) Activator Compound

The activator which is a second essential component of the photoinitiation system in the composition of the present invention is described below. The activator for use in the present invention is a compound of undergoing chemical change through interaction with an electronic excitation state of the sensitizing dye and producing at least any one of a radical, an acid and a base. Hereinafter, the radical, acid and base produced in this way are simply referred to as an active species. If such a compound is not present or the activator is used alone, practically sufficient sensitivity cannot be obtained, but, as one embodiment of using the above-described sensitizing dye and the activator compound in combination, these may be used as a single compound by employing an appropriate chemical method (for example, linkage of the sensitizing dye and the activator compound by chemical bonding). Such a technical idea is disclosed, for example, in Japanese Patent 2,720,195.

Most of these activators are considered to generally produce an active species through the following initial chemical processes (1) to (3), that is, (1) reductive decomposition of the activator, based on the electron transfer reaction from the electronic excitation state of the sensitizing dye to the activator, (2) oxidative decomposition of the activator, based on the electron transfer from the activator to the electronic excitation state of the sensitizing dye and (3) decomposition of the activator from its electronic excitation state, based on the energy transfer from the electronic excitation state of the sensitizing dye to the activator. Although which activator compound belongs to which type of (1) to (3) is not clearly known in many cases, a remarkable characteristic feature of the sensitizing dye of the present invention is that whichever type of these activators is combined, the sensitizing dye exerts very high sensitization effect.

The activator compounds known to those skilled in the art can be used without limitation, and many compounds are specifically described, for example, in Bruce M. Monroe et al., *Chemical Review*, 93, 435 (1993), R. S. Davidson, *Journal of Photochemistry and Biology A: Chemistry*, 73.81 (1993), J. P. Faussier, *Photoinitiated Polymerization-Theory and Applications: Rapra Review*, vol. 9, Report, Rapra Technology (1998), and M. Tsunooka et al., *Prog. Polym. Sci.*, 21, 1 (1996). Other known compounds having a function of (1) or (2) above include compounds of undergoing oxidative or reductive bond cleavage described, for example, in F. D. Saeva, *Topics in Current Chemistry*, 156, 59 (1990), G. G. Maslak, *Topics in Current Chemistry*, 168, 1 (1993), H. B. Shuster et al., *JACS*, 112, 6329 (1990), and I. D. F. Eaton et al., *JACS*, 102, 3298 (1980).

In the following, preferred activators are specifically described by classifying these into (a) an activator of producing an active species by undergoing bond cleavage when reduced, (b) an activator of producing an active species by undergoing bond cleavage when oxidized, and (c) others, however, accepted views are not present in many cases regarding which compound belongs to which group of this classification and the present invention is not restricted by the description on these reaction mechanisms.

(a) Activator of Producing Active Species by Undergoing Bond Cleavage when Reduced Compound having Carbon-Halogen Bond:

This compound is considered to generate an active species resulting from reductive cleavage of carbon-halogen bond (described, for example, in *Polymer Preprints, Jpn.*, 41 (3), 542 (1992)). The active species which can be generated is a radical or an acid. Specific examples of the compound which can be suitably used include halomethyl-s-triazines, halomethyloxadiazoles (which can be easily synthesized by one skilled in the art according to the synthetic method described in M. P. Hutt, E. F. Elslager and L. M. Merbel, *Journal of Heterocyclic Chemistry*, 7, 511 (1970)) and compounds described in German Patents 2,641,100, 3,333,450, 3,021,590 and 3,021,599.

Compound having Nitrogen-Nitrogen Bond or Nitrogen-Containing Heterocyclic Ring-Nitrogen-Containing Hetero-Cyclic Ring Bond:

This compound causes reductive bond cleavage (described, for example, in *J. Pys. Chem.*, 96, 207 (1992)). Specific examples of the compound which can be suitably used include hexaarylbiimidazoles. The active species generated is a lophine radical and this radical initiates a radical chain reaction when used, if desired, in combination with a hydrogen donor. Also, image formation using an oxidation reaction by the lophine radical is known (described, for example, in *J. Imaging Sci.*, 30, 215 (1986)).

Compound having Oxygen-Oxygen Bond:

This compound is considered to generate an active radical resulting from reductive cleavage of oxygen-oxygen bond (described, for example, in *Polym. Adv. Technol.*, 1, 287 (1990)). Specific examples of the compound which can be suitably used include organic peroxides. The active species which can be generated is a radical.

Onium Compound:

This compound is considered to generate an active species resulting from reductive cleavage of carbon-hetero bond or oxygen-nitrogen bond (described, for example, in *J. Photopolym. Sci. Technol.*, 3, 149 (1990)). Specific examples of the compound which can be suitably used include iodonium salts described in European Patent 104143, U.S. Pat. No. 4,837,124, JP-A-2-150848 and JP-A-2-96514, sulfonium salts described in European Patents 370693, 233567, 297443, 297442, 279210 and 422570, U.S. Pat. Nos. 3,902,144, 4,933,377, 4,760,013, 4,734,444 and 2,833,827, diazonium salts (e.g., benzenediazonium which may have a substituent), diazonium salt resins (e.g., formaldehyde resin of diazodiphenylamine), N-alkoxypyridinium salts (e.g., those described in U.S. Pat. No. 4,743,528, JP-A-63-138345, JP-A-63-142345, JP-A-63-142346 and JP-B-46-42363, specifically, 1-methoxy-4-phenylpyridinium tetrafluoroborate) and compounds described in JP-B-52-147277, JP-B-52-14278 and JP-B-52-14279. The active species which is generated is a radical or an acid.

Active Esters:

For example, nitrobenzyl esters of sulfonic acid or carboxylic acid, esters of sulfonic acid or carboxylic acid with N-hydroxy compound (e.g., N-hydroxyphthalimide, oxime), sulfonic acid esters of pyrogallol and naphthoquinone-diazido-4-sulfonic acid esters can be reductively decomposed. The active species which can be generated is a radical or an acid. Specific examples of the sulfonic acid esters include nitrobenzyl ester compounds described in European Patents 0290750, 046083, 156153, 271851 and 0388343, U.S. Pat. Nos. 3,901,710 and 4,181,531, JP-A-60-198538 and JP-A-53-133022, iminosulfonate compounds described in European Patents 0199672, 84515, 199672, 044115 and 0101122, U.S. Pat. Nos. 4,618,564, 4,371,605 and 4,431,774, JP-A-64-18143, JP-A-2-245756 and JP-A-4-365048 and compounds described in JP-B-62-6223, JP-B-63-14340 and JP-A-59-174831. Other examples include compounds shown below.

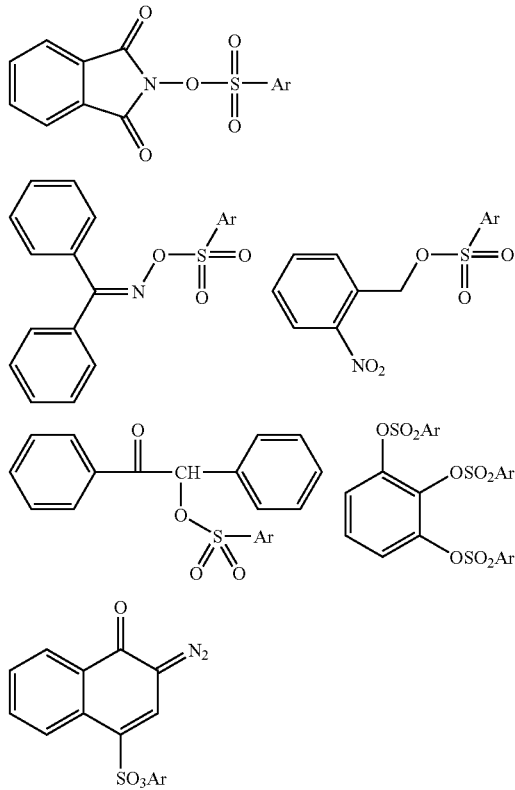

(wherein Ar represents an aromatic or aliphatic group which may be substituted).

Also, a base can be produced as the active species and, for example, the following compounds are known.

Ferrocene and Iron Arene Complexes:

These can reductively produce an active radical. These are specifically disclosed, for example, in JP-A-1-304453 and JP-A-1-152109.

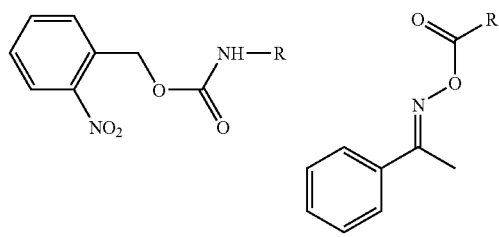

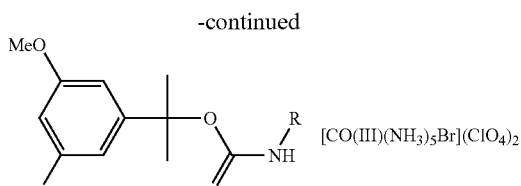

(wherein R represents an aliphatic or aromatic group which may be substituted).

Disulfones:

These can generate an acid by causing reductive cleavage of S—S bond. For example, diphenyldisulfones described in JP-A-61-166544 are known.

(b) Activators of Producing Active Species by undergoing Bond Cleavage when Oxidized Alkylate Complex:

This is considered to produce an active radical resulting from oxidative cleavage of carbon-hetero bond (described, for example, in *J. Am. Chem. Soc.*, 112, 6329 (1990)). Specific examples of the complex which can be suitably used include triaryl alkylborates.

Alkylamine Compound:

This compound is considered to produce an active radical resulting from oxidative cleavage of C—X bond on the carbon adjacent to nitrogen (described, for example, in *J. Am. Chem. Soc.*, 116, 4211 (1994)). X is suitably a hydrogen atom, a carboxyl group, a trimethylsilyl group, a benzyl group or the like. Specific examples of the compound include ethanolamines, N-phenylglycines and N-trimethylsilylmethylanilines.

Sulfur- or Tin-Containing Compound:

Those resulting from replacing a nitrogen atom of the above-described amines by a sulfur atom or a tin atom can produce an active radical by the same operation. Also, compounds having S—S bond are known to effect sensitization by S—S cleavage.

α-Substituted Methylcarbonyl Compound:

This compound can produce an active radical resulting from oxidative cleavage of carbonyl-α carbon bond. A compound where carbonyl is converted into an oxime ether also shows the same activity. Specific examples of the compound include 2-alkyl-1-[4-(alkylthio)phenyl]-2-morpholinopulonone-1 compounds and oxime ethers obtained by reacting these compounds with hydroxyamines and then etherifying N—OH.

Sulfinic Acid Salts:

These salts can reductively produce an active radical. Specific examples thereof include sodium arylsulfinate.

(c) Others

Although the sensitization mechanism is not clear, many compounds can function as an activator. Specific examples thereof include organic metal compounds such as titanocene, aromatic ketones, acylphosphines and biacylphosphines. The active species which can be generated is a radical or an acid.

Among the activator compounds for use in the present invention, preferred compounds having excellent sensitivity and stability are specifically described below.

(1) Halomethyltriazines

A compound represented by the following formula [I] is included and this compound is particularly excellent in the ability of generating a radical or an acid.

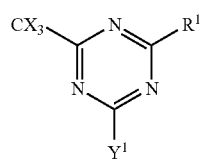

[I]

wherein X represents a halogen atom, $Y^1$ represents —$CX_3$, —$NH_2$, —$NHR^{1'}$, $N(R^{1'})_2$ or —$OR^{1'}$ (wherein $R^{1'}$ represents an alkyl group, a substituted alkyl group, an aryl group or a substituted aryl group), and $R^1$ represents —$CX_3$, an alkyl group, a substituted alkyl group, an aryl group, a substituted aryl group or a substituted alkenyl group.

Specific examples of this compound include compounds described in Wakabayashi et al., *Bull. Chem. Soc. Japan*, 42, 2924 (1969), such as 2-phenyl-4,6-bis(trichloromethyl)-S-triazine, 2-(p-chlorophenyl)-4,6-bis(trichloromethyl)-S-triazine, 2-(p-tolyl)-4,6-bis(trichloromethyl)-S-triazine, 2-(p-methoxyphenyl)-4,6-bis(trichloromethyl)-S-triazine, 2-(2',4'-dichlorophenyl)-4,6-bis(trichloromethyl)-S-triazine, 2,4,6-tris(trichloromethyl)-S-triazine, 2-methyl-4,6-bis(trichloromethyl)-S-triazine, 2-n-nonyl-4,6-bis(trichloromethyl)-S-triazine and 2-(α,α,β-trichloroethyl)-4,6-bis(trichloromethyl)-S-triazine. Other examples include compounds described in British Patent 1,388,492, such as 2-(styryl-4,6-bis(trichloromethyl)-S-triazine, 2-(p-methylstyryl)-4,6-bis(trichloromethyl)-S-triazine, 2-(p-methoxystyryl)-4,6-bis(trichloromethyl)-S-triazine and 2-(p-methoxystyryl)-4-amino-6-trichloromethyl-S-triazine, compounds described in JP-A-53-133428, such as 2-(4-methoxy-naphtho-1-yl)-4,6-bis-trichloromethyl-S-triazine, 2-(4-ethoxy-naphtho-1-yl)-4,6-bis-trichloromethyl-S-triazine, 2-[4-(2-ethoxyethyl)-naphtho-1-yl]-4,6-bis-trichloromethyl-S-triazine, 2-(4,7-dimethoxy-naphtho-1-yl)-4,6-bis-trichloromethyl-S-triazine and 2-(acenaphtho-5-yl)-4,6-bis-trichloromethyl-S-triazine, and compounds described in German Patent 3,337,024, such as compounds shown below.

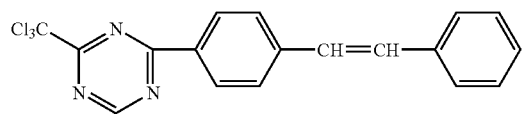

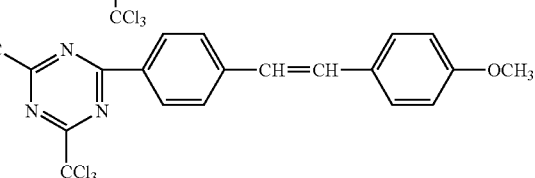

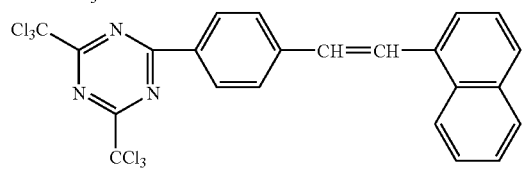

-continued

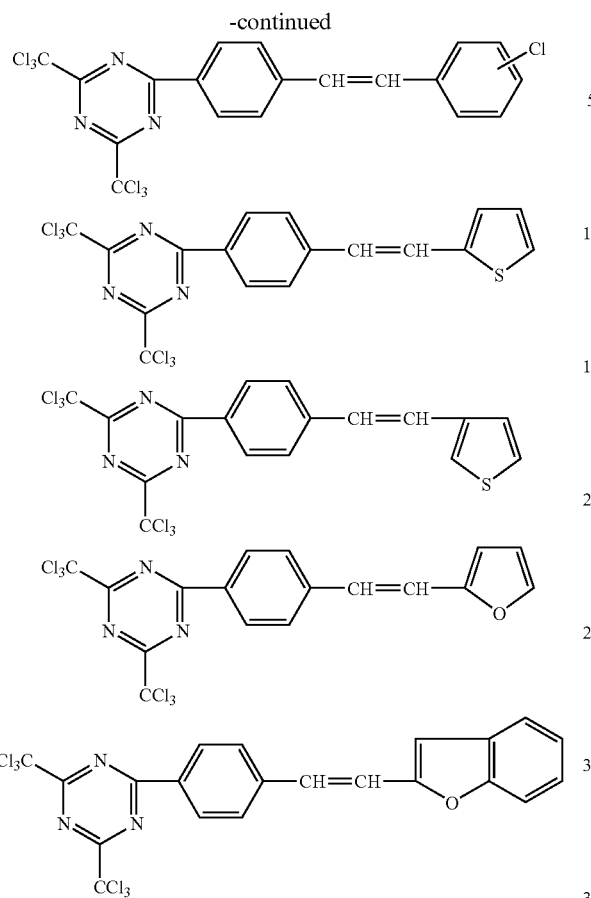

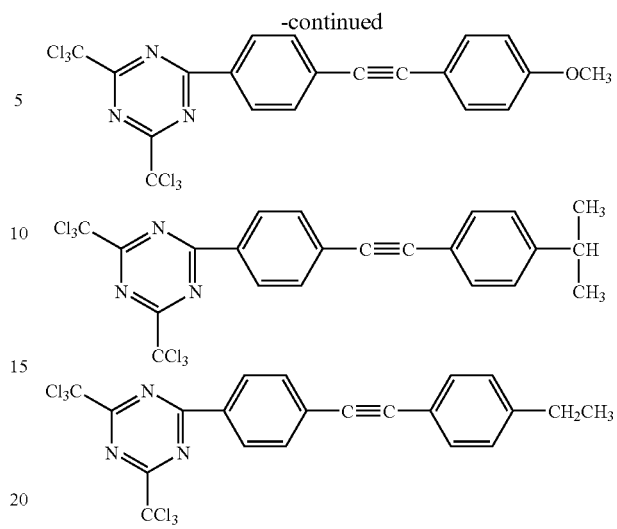

Other examples include compounds described in F. C. Schaefer et al., *J. Org. Chem.*, 29, 1527 (1964), such as 2-methyl-4,6-bis(tribromomethyl)-S-triazine, 2,4,6-tris-(tribromomethyl)-S-triazine, 2,4,6-tris(dibromomethyl)-S-triazine, 2-amino-4-methyl-6-tribromomethyl-S-triazine and 2-methoxy-4-methyl-6-trichloromethyl-S-triazine.

Other examples include compounds described in JP-A-62-58241, such as compounds shown below.

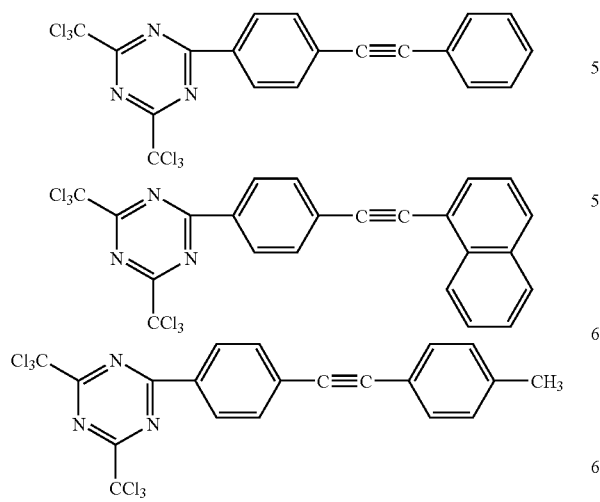

Other examples include compounds described in JP-A-5-281728, such as compounds shown below.

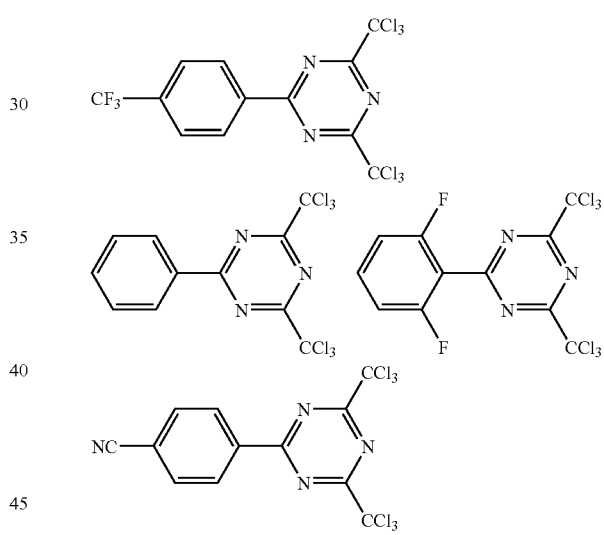

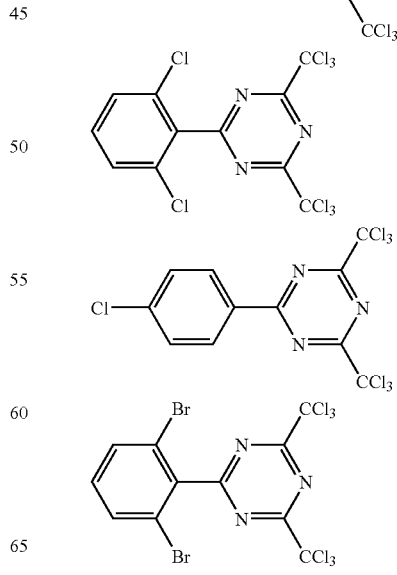

(2) Titanocenes

The titanocene compound which is particularly preferably used as the activator may be any titanocene compound as long as it can generate an active species when irradiated with light in the presence of the above-described sensitizing dye together. For example, known compounds described in JP-A-59-152396, JP-A-61-151197, JP-A-63-41483, JP-A-63-41484, JP-A-2-249, JP-A-2-291, JP-A-3-27393, JP-A-3-12403 and JP-A-6-41170 can be appropriately selected and used.

Specific examples thereof include dicyclopentadienyl-Ti-dichloride, dicyclopentadienyl-Ti-bisphenyl, dicyclo-pentadienyl-Ti-bis-2,3,4,5,6-pentafluorophen-1-yl, dicyclo-pentadienyl-Ti-bis-2,3,5,6-tetrafluorophen-1-yl, dicyclopentadienyl-Ti-bis-2,4,6-trifluorophen-1-yl, dicyclopentadienyl-Ti-bis-2,6-difluorophen-1-yl, dicyclopentadienyl-Ti-bis-2,4-difluorophen-1-yl, dimethylcyclopentadienyl-Ti-bis-2,3,4,5,6-pentafluorophen-1-yl, dimethylcyclopentadienyl-Ti-bis-2,3,5,6-tetrafluorophen-1-yl, dimethylcyclopentadienyl-Ti-bis-2,4-difluorophen-1-yl and bis(cyclopentadienyl)-bis(2,6-difluoro-3-(pyr-1-yl)phenyl)titanium.

(3) Borate Salt Compounds

The borate salts represented by the following formula [II] have excellent radical generation ability.

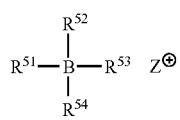
[II]

wherein $R^{51}$, $R^{52}$, $R^{53}$ and $R^{54}$ may be the same or different and each represents a substituted or unsubstituted alkyl group, a substituted or unsubstituted aryl group, a substituted or unsubstituted alkenyl group, a substituted or unsubstituted alkynyl group or a substituted or unsubstituted heterocyclic group, two or more groups of $R^{51}$, $R^{52}$, $R^{53}$ and $R^{54}$ may combine to form a cyclic structure, with the proviso that at least one of $R^{51}$, $R^{52}$, $R^{53}$ and $R^{54}$ is a substituted or unsubstituted alkyl group, and $Z^+$ represents an alkali metal cation or a quaternary ammonium cation.

The alkyl group of $R^{51}$ to $R^{54}$ includes a straight, branched or cyclic alkyl group and is preferably an alkyl group having from 1 to 18 carbon atoms. Specific examples thereof include methyl, ethyl, propyl, isopropyl, butyl, pentyl, hexyl, octyl, stearyl, cyclobutyl, cyclopentyl and cyclohexyl. Examples of the substituted alkyl group include the above-described alkyl groups which are substituted by a halogen atom (e.g., —Cl, —Br), a cyano group, a nitro group, an aryl group (preferably a phenyl group), a hydroxy group, a group shown below:

(wherein $R^{55}$ and $R^{56}$ each independently represents a hydrogen atom, an alkyl group having from 1 to 14 carbon atoms or an aryl group), —COOR$^{57}$ (wherein $R^{57}$ represents a hydrogen atom, an alkyl group having from 1 to 14 carbon atoms or an aryl group), —COOR$^{58}$ or —OR$^{59}$ (wherein $R^{58}$ and $R^{59}$ each represents an alkyl group having from 1 to 14 carbon atoms or an aryl group).

The aryl group of $R^{51}$ to $R^{54}$ includes an aryl group having from 1 to 3 rings, such as phenyl group and naphthyl group, and examples of the substituted aryl group include an aryl group having a substituent described above for the substituted alkyl group and an aryl group substituted by an alkyl group having from 1 to 14 carbon atoms.

The alkenyl group of $R^{51}$ to $R^{54}$ includes a straight, branched or cyclic alkenyl group having from 2 to 18 carbon atoms, and examples of the substituent of the substituted alkenyl group include those described above as the substituent of the substituted alkyl group.

The alkynyl group of $R^{51}$ to $R^{54}$ includes a straight or branched alkynyl group having from 2 to 28 carbon atoms, and examples of the substituent of substituted alkynyl group include those described above as the substituent of the substituted alkyl group.

The heterocyclic group of $R^{51}$ to $R^{54}$ includes a 5- or more membered heterocyclic group containing at least one of N, S and O, preferably a 5-, 6- or 7-membered ring, and the heterocyclic ring may contain a condensed ring and also may have a substituent selected from those described above as the substituent of the substituted aryl group.

Specific examples of the compound represented by formula [II] include compounds described in U.S. Pat. Nos. 3,567,453 and 4,343,891 and European Patents 109772 and 109773, and compounds shown below.

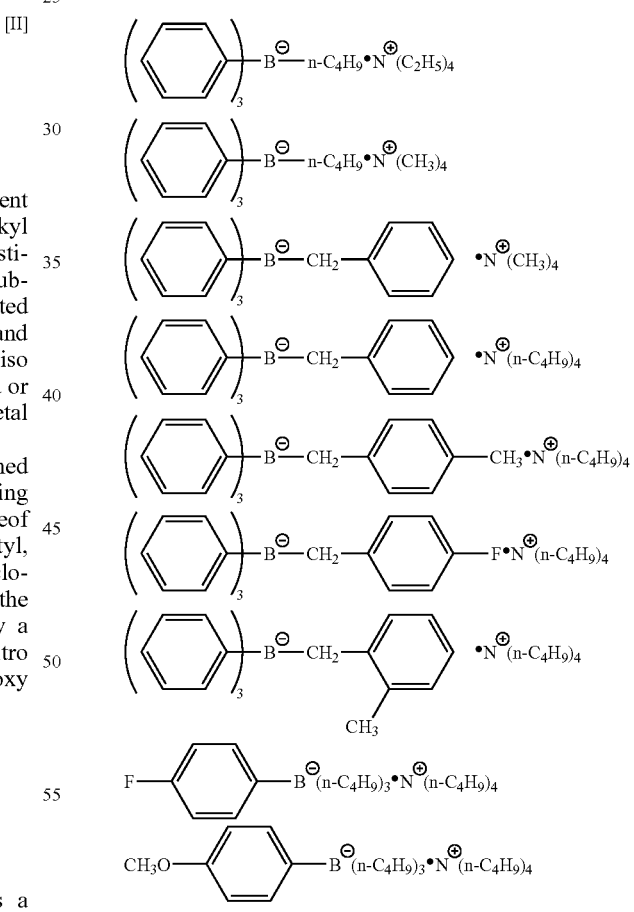

(4) Hexaarylbiimidazoles

Hexaarylbiimidazoles have excellent stability and can perform radical generation with high sensitivity.

Specific examples thereof include 2,2'-bis(o-chlorophenyl)-4,4',5,5'-tetraphenylbiimidazole, 2,2'-bis(o-bromophenyl)-4,4',5,5'-tetraphenylbiimidazole, 2,2'-bis(o,p-dichlorophenyl)-4,4',5,5'-tetraphenylbiimidazole, 2,2'-bis(o-chlorophenyl)-4,4',5,5'-tetra(m-methoxyphenyl)-biimidazole, 2,2'-bis(o,o'-dichlorophenyl)-4,4',5,5'-tetraphenylbiimidazole, 2,2'-bis(o-nitrophenyl)-4,4',5,5'-tetraphenylbiimidazole, 2,2'-bis(o-methylphenyl)-4,4',5,5,-tetraphenylbiimidazole and 2,2'-bis(o-trifluoromethylphenyl)-4,4',5,5'-tetraphenylbiimidazole.

(5) Onium Salt Compound

Onium compounds of elements belonging to Group 15(5B), 16(6B) and 17(7B) in the Periodic Table, specifically N, P, As, Sb, Bi, O, S, Se, Te and I, are activators having excellent sensitivity. Among these, iodonium salts and sulfonium salts, particularly diaryliodonium and triarylsulfonium salt compounds, are very excellent in view of both sensitivity and storage stability. These compounds can generate an acid and/or a radical, and a proper compound can be used by appropriately selecting the conditions on use according to the purpose. Specific examples thereof include the following compounds.

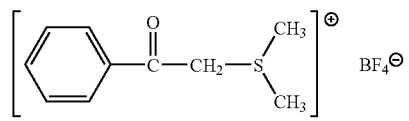

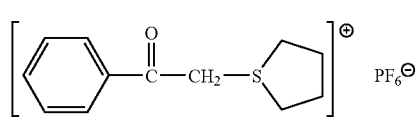

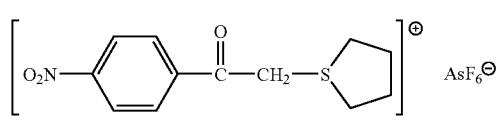

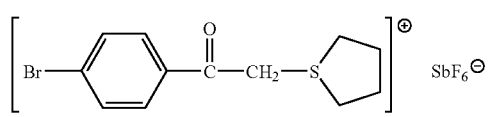

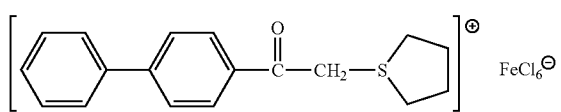

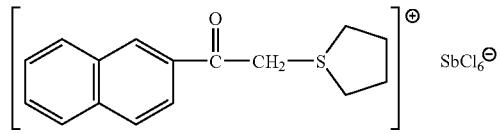

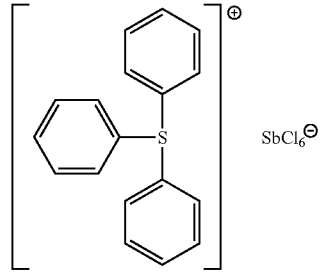

-continued

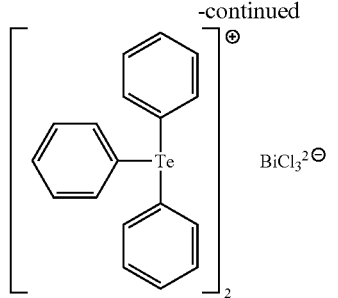

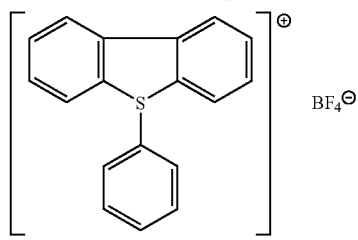

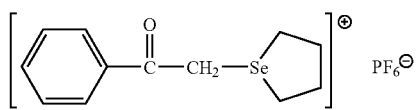

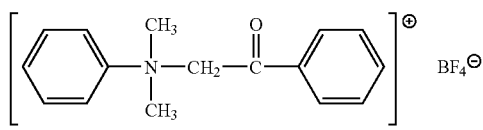

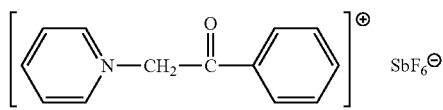

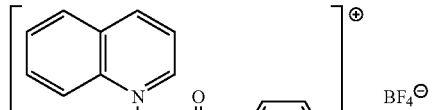

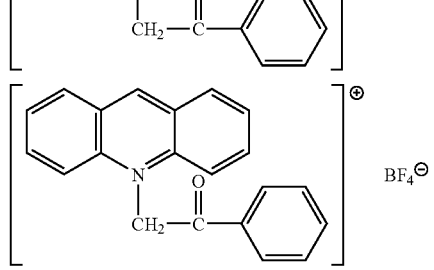

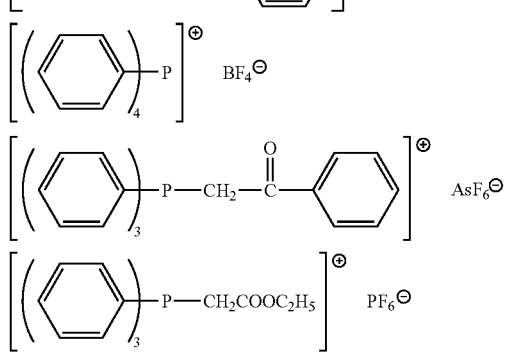

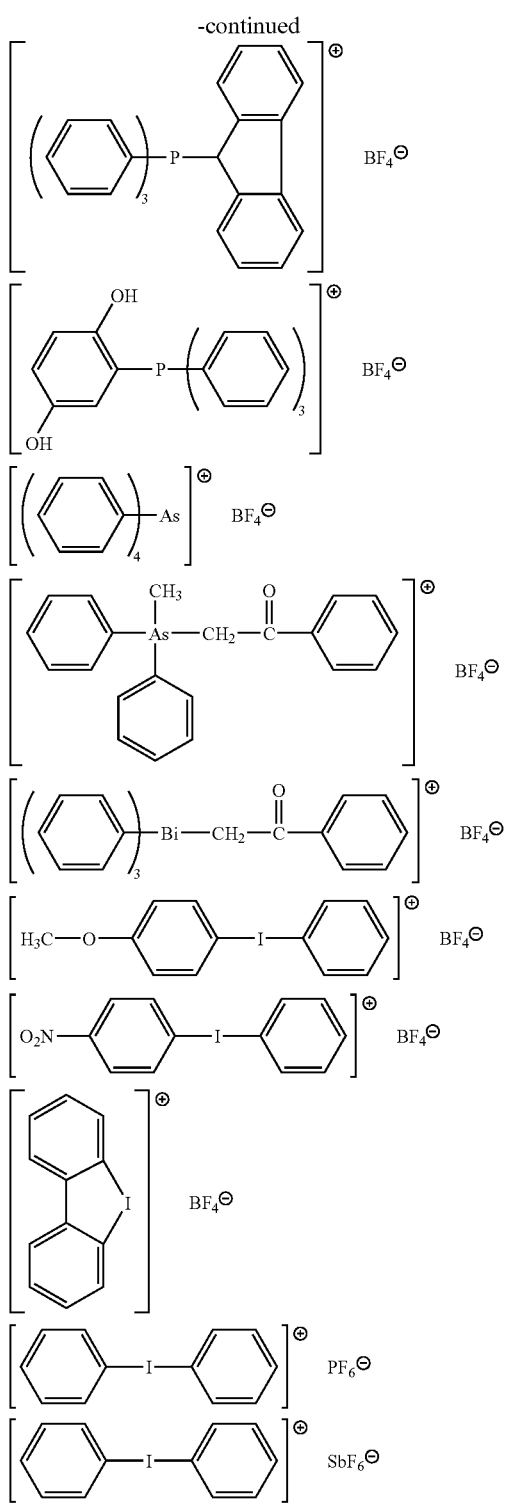

(6) Organic Peroxide

In the case of using an organic peroxide-type activator, a radical as the active species can be generated with very high sensitivity.

The "organic peroxide" includes almost all organic compounds having one or more oxygen-oxygen bond within the molecule, and examples thereof include methyl ethyl ketone peroxide, cyclohexanone peroxide, 3,3,5-trimethylcyclohexanone peroxide, methylcyclohexanone peroxide, acetylacetone peroxide, 1,1-bis(tert-butylperoxy)-3,3,5-trimethylcyclohexane, 1,1-bis(tert-butylperoxy)cyclohexane, 2,2-bis(tert-butylperoxy)butane, tert-butyl hydroperoxide, cumene hydroperoxide, diisopropylbenzene hydroperoxide, paramethane hydroperoxide, 2,5-dimethylhexane-2,5-dihydro-peroxide, 1,1,3,3-tetramethylbutyl hydroperoxide, di-tert-butyl peroxide, tert-butylcumyl peroxide, dicumyl peroxide, bis(tert-butylperoxyisopropyl)benzene, 2,5-dimethyl-2,5-di(tert-butylperoxy)hexane, 2,5-dimethyl-2,5-di(tert-butylperoxy)hexyne-3, acetyl peroxide, isobutyryl peroxide, octanoyl peroxide, decanoyl peroxide, lauroyl peroxide, 3,5,5-trimethylhexanoyl peroxide, succinic acid peroxide, benzoyl peroxide, 2,4-dichlorobenzoyl peroxide, metatoluoyl peroxide, diisopropyl peroxydicarbonate, di-2-ethylhexyl peroxydicarbonate, di-2-ethoxyethyl peroxydicarbonate, dimethoxyisopropyl peroxycarbonate, di(3-methyl-3-methoxybutyl) peroxydicarbonate, tert-butyl peroxyacetate, tert-butyl peroxypivalate, tert-butyl peroxyneodecanoate, tert-butyl peroxyoctanoate, tert-butyl peroxy-3,5,5-trimethylhexanoate, tert-butyl peroxylaurate, tert-butyl peroxybenzoate, di-tert-butyl peroxyisophthalate, 2,5-dimethyl-2,5-di(benzoylperoxy)hexane, tert-butyl peroxymaleate, tert-butyl peroxyisopropylcarbonate, 3,3',4,4'-tetra(tert-butylperoxycarbonyl)benzophenone, 3,3',4,4'-tetra(tert-amylperoxycarbonyl)benzophenone, 3,3',4,4'-tetra(tert-hexylperoxycarbonyl)benzophenone, 3,3',4,4'-tetra(tert-octylperoxycarbonyl)benzophenone, 3,3',4,4'-tetra(cumylperoxycarbonyl)benzophenone, 3,3',4,4'-tetra(p-isopropylcumylperoxycarbonyl)benzophenone, carbonyl di(tert-butylperoxydihydrogendiphthalate) and carbonyl di(tert-hexylperoxydihydrogendiphthalate).

Among these, preferred are peroxide ester-type compounds such as 3,3',4,4'-tetra(tert-butylperoxy-carbonyl) benzophenone, 3,3',4,4'-tetra(tert-amylperoxycarbonyl)benzophenone, 3,3',4,4'-tetra(tert-hexylperoxycarbonyl)benzophenone, 3,3',4,4'-tetra(tert-octylperoxycarbonyl)benzophenone, 3,3',4,4'-tetra(cumylperoxycarbonyl)benzophenone, 3,3',4,4'-tetra-(p-isopropylcumylperoxycarbonyl)benzophenone and di-tert-butyl diperoxyisophthalate.

Among these activators, particularly preferred are (1) halomethyltriazines and (2) titanocenes.

Similarly to the above-described sensitizing dye, these activators can also be subjected to various chemical modifications for the purpose of improving the properties of the photosensitive layer. Examples of the method which can be used therefor include binding to the sensitizing dye, addition-polymerizable unsaturated compound or other activator parts, introduction of a hydrophilic moiety, introduction of a substituent for improving compatibility and inhibiting crystallization or for enhancing adhesion, and formation into a polymer.

Also, similarly to the above-described sensitizing dyes, the use method of these activator compounds can be appropriately and arbitrarily set according to the performance design of the photosensitive material. For example, the compatibility in the photosensitive layer can be enhanced by using two or more activator compounds in combination. Generally, the amount of the activator compound used is preferably larger in view of photosensitivity, and sufficiently high photosensitivity can be obtained by using the activator compound in an amount of 0.5 to 80 parts by mass, preferably from 1 to 50 parts by mass, per 100 parts by mass of the photosensitive layer components. On the other hand, in the case where the activator itself has absorption in the visible light region like a titanocene compound, the amount of the activator used is preferably smaller on use under yellow or white light in view of fog due to light in the vicinity of 500 nm, but by the combination with the sensitizing dye of the present invention, sufficiently high photosensitivity can be obtained even when the amount of the activator compound used is decreased to 6 parts by mass or less, further to 1.9 parts by mass or less, even to 1.4 parts by mass or less.

B. Component (iii)

The third essential component (iii) in the composition of the present invention is a compound which undergoes irreversible change in the physical or chemical property under the action of the above-described active species produced by a photoreaction of the photoinitiation system, and an arbitrary compound can be used for the component (iii) without particular limitation as long as it has such property. For example, the compounds described above in regard to the initiation system have such property in many cases. The change in the property of the component (iii), which is caused under the action of either a radical or an acid produced from the photoinitiation system, include change in the physical property from molecular aspect, such as absorption spectrum (color), chemical structure and polarizability, and change in the physical property from material aspect, such as solubility, strength, refractive index, fluidity and adhesive property.

For example, when a compound of undergoing change in the absorption spectrum by pH, such as pH indicator, is used as the component (iii) and an acid or base is generated from the initiation system, color tone only in the exposed area can be changed and such a composition is useful as an image-forming material. Also, when a compound of undergoing change in the absorption spectrum by an oxidation-reduction or nucleophilic addition reaction is used as the component (iii), a reaction such as oxidation or reduction is induced by the radical generated from the initiation system and an image can be formed. This is disclosed, for example, in *J. Am. Chem. Soc.*, 108, 128 (1986), *J. Imaging. Sci.*, 30, 215 (1986), and *Israel. J. Chem.*, 25, 264 (1986).

Also, when an addition-polymerizable or polycondensation-polymerizable compound is used as the component (iii) and combined with the initiation system, a photocurable resin or a negative photopolymer can be formed.

As the component (iii), radical-polymerizable compounds (e.g., a compound having an ethylenic unsaturated bond), cationic-polymerizable compounds (e.g., epoxy compound, vinyl ether compound, methylol compound) and anionic-polymerizable compounds (e.g., epoxy compound) are used, and these are described, for example, in *Photopolymer Handbook*, compiled by Photopolymer Konwa Kai, Kogyo Chosa Kai (1989), and *Kobunshi (Polymer)*, 45, 786 (1996). Also, a composition where a thiol compound is used as the component (iii) and combined with a photoradical generation system is well known.

It is also effective to use an acid-decomposable compound as the component (iii) and combine it with a photoacid generator. For example, a material which uses a polymer having an acid-decomposable side or main chain and undergoes change in the solubility or hydrophilic or hydrophobic property by light is widely used in practice as a photodecomposable photosensitive resin or a positive photopolymer. Specific examples thereof are described, for example, in *ACS. Symp. Ser.*, 242, 11 (1984), JP-A-60-3625, U.S. Pat. Nos. 5,102,771, 5,206,317 and 5,212,047, JP-A-4-26850, JP-A-3-1921731, JP-A-60-10247 and JP-A-62-40450.

The addition-polymerizable compound having an ethylenic unsaturated double bond, which is a particularly excellent component (iii) for obtaining a high-sensitivity lithographic printing plate as one object of the present invention, is described in more detail below.

(B-1) Addition-Polymerizable Compound

The addition-polymerizable compound having at least one ethylenic unsaturated double bond, which is a preferred component (iii) for use in the present invention, is selected from compounds having at least one, preferably two or more, terminal ethylenic unsaturated double bond. These compounds are widely known in this industrial field and can be used in the present invention without particular limitation. These compounds have a chemical form such as monomer, prepolymer (namely, dimer, trimer or oligomer) or a mixture or copolymer thereof. Examples of the monomer and a copolymer thereof include unsaturated carboxylic acids (e.g., acrylic acid, methacrylic acid, itaconic acid, crotonic acid, isocrotonic acid, maleic acid), and esters and amides thereof. Among these, preferred are esters of an unsaturated carboxylic acid with an aliphatic polyhydric alcohol compound, and amides of an unsaturated carboxylic acid with an aliphatic polyvalent amine compound. A reaction product of an unsaturated carboxylic acid ester or amide having a nucleophilic substituent (e.g., hydroxyl group, amino group, mercapto group), such as addition reaction product with a monofunctional or polyfunctional isocyanate or an epoxy compound, and dehydrating condensation reaction product with a monofunctional or polyfunctional carboxylic acid, is also suitably used. Furthermore, an addition product of an unsaturated carboxylic acid ester or amide having an electrophilic substituent such as isocyanato group or epoxy group with a monofunctional or polyfunctional alcohol, amine or thiol, and a displacement reaction product of an unsaturated carboxylic acid ester or amide having a splitting-off substituent such as halogen group or tosyloxy group with a monofunctional or polyfunctional alcohol, amine or thiol are also suitably used. Other than these, compounds obtained by replacing the unsaturated carboxylic acid in these compounds by an unsaturated phosphonic acid, styrene, a vinyl ether or the like can also be used.

With respect to the ester monomer of an aliphatic polyhydric alcohol compound with an unsaturated carboxylic acid, specific examples of the acrylic acid ester include ethylene glycol diacrylate, triethylene glycol diacrylate, 1,3-butanediol diacrylate, tetramethylene glycol diacrylate, propylene glycol diacrylate, neopentyl glycol diacrylate, trimethylolpropane triacrylate, trimethylolpropane tri(acryloyloxypropyl) ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol hexaacrylate, sorbitol triacrylate, sorbitol tetraacrylate, sorbitol pentaacrylate, sorbitol hexaacrylate, tri(acryloyloxyethyl) isocyanurate and polyester acrylate oligomer.

Examples of the methacrylic acid ester include tetramethylene glycol dimethacrylate, triethylene glycol dimethacrylate, neopentyl glycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, sorbitol trimethacrylate, sorbitol tetramethacrylate, bis[p-(3-methacryloxy-2-hydroxypropoxy)-phenyl]dimethylmethane and bis[p-(methacryloxyethoxy)-phenyl]dimethylmethane.

Examples of the itaconic acid ester include ethylene glycol diitaconate, propylene glycol diitaconate, 1,3-butanediol diitaconate, 1,4-butanediol diitaconate, tetramethylene glycol diitaconate, pentaerythritol diitaconate and sorbitol tetraitaconate.

Examples of the crotonic acid ester include ethylene glycol dicrotonate, tetramethylene glycol dicrotonate, pentaerythritol dicrotonate and sorbitol tetradicrotonate.

Examples of the isocrotonic acid ester include ethylene glycol diisocrotonate, pentaerythritol diisocrotonate and sorbitol tetraisocrotonate.

Examples of the maleic acid ester include ethylene glycol dimaleate, triethylene glycol dimaleate, pentaerythritol dimaleate and sorbitol tetramaleate.

Other examples of the ester which can be suitably used include aliphatic alcohol-base esters described in JP-B-46-27926, JP-B-51-47334 and JP-A-57-196231, those having an aromatic nucleus described in JP-A-59-5240, JP-A-59-5241 and JP-A-2-226149, and those containing an amino group described in JP-A-1-165613.

These ester monomers can be used as a mixture.

Specific examples of the amide monomer of an aliphatic polyhydric amine compound with an unsaturated carboxylic acid include methylenebis-acrylamide, methylenebis-methacrylamide, 1,6-hexamethylenebisacrylamide, 1,6-hexamethylenebis-methacrylamide, diethylenetriaminetrisacrylamide, xylylenebisacrylamide and xylylenebismethacrylamide.

Other preferred examples of the amide-base monomer include those having a cyclohexylene structure described in JP-B-54-21726.

A urethane-base addition-polymerizable compound produced by using an addition reaction of an isocyanate with a hydroxyl group is also suitably used, and specific examples thereof include vinyl urethane compounds having two or more polymerizable vinyl groups within one molecule described in JP-B-48-41708, which is produced by adding a hydroxyl group-containing vinyl monomer represented by the following formula (III) to a polyisocyanate compound having two or more isocyanate groups within one molecule:

CH$_2$=C(R)COOCH$_2$CH(R')OH　　(III)

(wherein R and R' each represents H or CH$_3$).

Also, urethane acrylates described in JP-A-51-37193, JP-B-2-32293 and JP-B-2-16765 and urethane compounds having an ethylene oxide-base skeleton described in JP-B-58-49860, JP-B-56-17654, JP-B-62-39417 and JP-B-62-39418 are also suitably used.

Furthermore, when addition-polymerizable compounds having an amino structure or a sulfide structure within the molecule described in JP-A-63-277653, JP-A-63-260909 and JP-A-1-105238 are used, a photopolymerizable composition having very excellent sensitization speed can be obtained.

Other examples include polyfunctional acrylates and methacrylates such as polyester acrylates and epoxy acrylates obtained by reacting an epoxy resin with a (meth)acrylic acid described in JP-A-48-64183, JP-B-49-43191 and JP-B-52-30490. Also, specific unsaturated compounds described in JP-B-46-43946, JP-B-1-40337 and JP-B-1-40336 and vinylphosphonic acid-base compounds described in JP-A-2-25493 can be used. In some cases, a structure containing a perfluoroalkyl group described in JP-A-61-22048 is suitably used. In addition, those described as a photocurable monomer or oligomer in *Nippon Secchaku Kyokai Shi* (*Journal of the Adhesion Society of Japan*), Vol. 20, No. 7, pp. 300–308 (1984) can also be used.

On use of these addition-polymerizable compounds, details such as structure selected, single use or combination use, and amount added, can be arbitrarily set according to the performance design of the final photosensitive material. For example, the compound is selected by taking account of the following points. In view of the sensitization speed, a structure having a large unsaturated group content per one molecule is preferred, and in many cases, a bifunctional or greater functional group is preferred. For the purpose of increasing the strength of image area, namely, hardened film, a trifunctional or greater functional group is preferred. Furthermore, a method of adjusting both photosensitivity and strength by using compounds differing in the functional number and in the polymerizable group (for example, an acrylic ester, a methacrylic ester, a styrene-base compound or a vinyl ether-base compound) is also effective. A compound having a large molecular weight or high hydrophobic property is excellent in sensitization speed and film strength, but this compound is sometimes disadvantageous in view of development speed and precipitation in the developer. The selection and use method of the addition-polymerizable compound are important factors for the compatibility and dispersibility with other components (for example, binder polymer, initiator and colorant) in the photosensitive layer. For example, the compatibility may be improved by using a low purity compound or using two or more compounds in combination. Also, a specific structure may be selected for the purpose of improving the adhesive property of support, overcoat layer or the like. The ratio of the addition-polymerizable compound blended in the photosensitive layer is preferably larger in view of sensitivity, but if the blending ratio is excessively large, this may cause problems such as undesired phase separation, trouble in the production step due to adhesion of the photosensitive layer (for example, production failure ascribable to transfer or adhesion of the photosensitive material component), and precipitation from the developer. From these viewpoints, the blending ratio is in many cases from 5 to 80 mass %, preferably from 25 to 75 mass %, based on all components of the composition. These addition-polymerizable compounds may be used individually or in combination of two or more. As for the use method of the addition-polymerizable compound, appropriate structure, blending and amount added can be arbitrarily selected by taking account of the degree of polymerization inhibition by oxygen, resolution, fogging, change in the refractive index, surface adhesive property and the like. Depending on the case, the layer structure or coating method may contain undercoating or overcoating.

C. Binder Polymer

In the application to a lithographic printing plate which is a preferred embodiment of the present invention, a binder polymer is preferably further used in the photosensitive layer. The binder is preferably a linear organic high molecular polymer. The "linear organic high molecular polymer" may be any linear organic high molecular polymer, but a linear organic high molecular polymer soluble or swellable in water or a weak alkali solution is preferred and this enables development with water or a weak alkali solution. The linear organic high molecular polymer is used not only as a film-forming agent of the composition but also is selected according to use as a water, weak alkali solution or organic solvent developing agent. For example, when a water-soluble organic high molecular polymer is used, water development can be performed. Examples of such a linear organic high molecular polymer include addition polymers having a carboxylic acid group on the side chain described, for example, in JP-A-59-44615, JP-B-54-34327, JP-B-58-12577, JP-B-54-25957, JP-A-54-92723, JP-A-59-53836 and JP-A-59-71048, such as methacrylic acid copolymer, acrylic acid copolymer, itaconic acid copolymer, crotonic acid copolymer, maleic acid copolymer and partially esterified maleic acid copolymer. Also, acidic cellulose derivatives having a carboxylic acid group on the side chain may be used. Other than these compounds, those obtained by adding a cyclic acid anhydride to an addition polymer having a hydroxyl group are useful.

Among these, [benzyl (meth)acrylate/(meth)acrylic acid/ if desired, other addition-polymerizable vinyl monomer] copolymers and [allyl (meth)acrylate/(meth)acrylic acid/if desired, other addition-polymerizable vinyl monomer] copolymers are preferred because of their excellent balance in the film strength, sensitivity and developing property.

In addition, acid group-containing urethane-base binder polymers described, for example, in JP-B-7-12004, JP-B-7-120041, JP-B-7-120042, JP-B-8-12424, JP-A-63-287944, JP-A-63-287947, JP-A-1-271741 and Japanese Patent Application No. 10-116232 have very excellent strength and therefore, these are advantageous in view of press life and suitability for low exposure.

The amido group-containing binder described in JP-A-11-171907 is also preferred because this binder has both excellent developing property and film strength.

Furthermore, polyvinylpyrrolidone, polyethylene oxide and the like are useful as the water-soluble linear organic polymer. An alcohol-soluble nylon, a polyether of 2,2-bis-(4-hydroxyphenyl)-propane with epichlorohydrin, and the like are also useful for the purpose of increasing the strength of hardened film. The linear organic high molecular polymer can be mixed in an arbitrary amount in the entire composition. However, if the amount exceeds 90 mass %, an undesired effect results in view of image strength or the like. The amount mixed is preferably from 30 to 85 mass %. The photopolymerizable compound having an ethylenic unsaturated double bond and the linear organic high molecular polymer are preferably used at a mass ratio of 1/9 to 7/3. In a preferred embodiment, a binder polymer which is substantially insoluble in water and soluble in alkali is used. By using such a binder, the developer can use no or a very small amount of an organic solvent which is not preferred in view of environment. In such a use method, the acid value (an acid content per g of polymer, expressed by the chemical equivalent number) and molecular weight of the binder polymer are appropriately selected by taking account of the image strength and developability. The acid value is preferably from 0.4 to 3.0 meq/g and the molecular weight is preferably from 3,000 to 500,000 in terms of the weight average molecular weight. More preferably, the acid value is from 0.6 to 2.0 and the molecular weight is from 10,000 to 300,000.

D. Other Components

In the photosensitive composition of the present invention, other components suited for use, production method and the like can be appropriately added. Examples of preferred additives are described below.

(D1) Co-Sensitizer

The sensitivity can be more enhanced by using a certain additive (hereinafter, referred to as "co-sensitizer"). The operation mechanism of this additive is not clearly known but is considered to be based on the following chemical process in many cases. That is, the co-sensitizer is presumed to react with various intermediate active species (e.g., radical, peroxide, oxidizing agent, reducing agent) produced during the process of photo-reaction initiated by light absorption of the above-described initiation system and subsequent addition polymerization reaction, and produce a new active radical. These compounds are roughly classified into (a) a compound capable of producing an active radical when reduced, (b) a compound capable of producing an active radical when oxidized, and (c) a compound of reacting with a radical having low activity and converting it into a radical having higher activity or acting as a chain transfer agent. However, accepted views are not present in many cases regarding which compound belongs to which group of this classification.

(a) Compound of Producing Active Radical when Reduced

Compound having Carbon-Halogen Bond:

This compound is considered to generate an active radical resulting from reductive cleavage of carbon-halogen bond. Specific examples of the compound which can be suitably used include trihalomethyl-s-triazines and trihalomethyloxadiazoles.

Compound having Nitrogen-Nitrogen Bond:

This compound is considered to generate an active radical resulting from reductive cleavage of nitrogen-nitrogen bond. Specific examples of the compound which can be suitably used include hexaarylbiimidazoles.

Compound having Oxygen-Oxygen Bond:

This compound is considered to generate an active radical resulting from reductive cleavage of oxygen-oxygen bond. Specific examples of the compound which can be suitably used include organic peroxides.

Onium Compound:

This compound is considered to generate an active radical resulting from reductive cleavage of carbon-hetero bond or oxygen-nitrogen bond. Specific examples of the compound which can be suitably used include diaryliodonium salts, triarylsulfonium salts and N-alkoxypyridinium (azinium) salts.

Ferrocene and Iron Arene Complexes:

These can produce an active radical reductively.

(b) Compound of Producing Active Radical when Oxidized

Alkylate Complex:

This compound is considered to produce an active radical resulting from oxidative cleavage of carbon-hetero bond. Specific examples of the complex which can be suitably used include triaryl alkylborates.

Alkylamine Compound:

This compound is considered to produce an active radical resulting from oxidative cleavage of C—X bond on the carbon adjacent to nitrogen. X is suitably a hydrogen atom, a carboxyl group, a trimethylsilyl group, a benzyl group or the like. Specific examples of the compound include ethanolamines, N-phenylglycines and N-trimethyl-silylmethylanilines.

Sulfur- or Tin-Containing Compound:

A compound where the nitrogen atom of the above-described amines is replaced by a sulfur or tin atom can produce an active radical by the same operation. Also, a compound having S—S bond is known to effect sensitization by S—S cleavage.

α-Substituted Methylcarbonyl Compound:

This compound can produce an active radical resulting from oxidative cleavage of carbonyl-α carbon bond. A compound where the carbonyl is converted into an oxime ether also shows the same activity. Specific examples of the compound include 2-alkyl-1-[4-(alkylthio)phenyl]-2-morpholinopulonone-1 compounds and oxime ethers obtained by reacting these compounds with hydroxyamines and then etherifying N—OH.

Sulfinic Acid Salts:

These can produce an active radical reductively. Specific examples thereof include sodium arylsulfinate.

(c) Compound of Reacting with a Radical and Converting it into a Radical having Higher Activity or Acting as a Chain Transfer Agent For example, compounds having SH, PH, SiH or GeH within the molecule are used. These compounds can produce a radical by donating hydrogen to a radical species having low activity or produce a radical by being oxidized and then undergoing deprotonation. Specific examples of the compound include 2-mercaptobenzimidazoles.

Many examples of these co-sensitizers are more specifically described, for example, in JP-A-9-236913 as additives used for the purpose of improving sensitivity. Some of these compounds are shown below, but the present invention is not limited thereto. In the compounds shown below, -TMS represents a trimethylsilyl group.

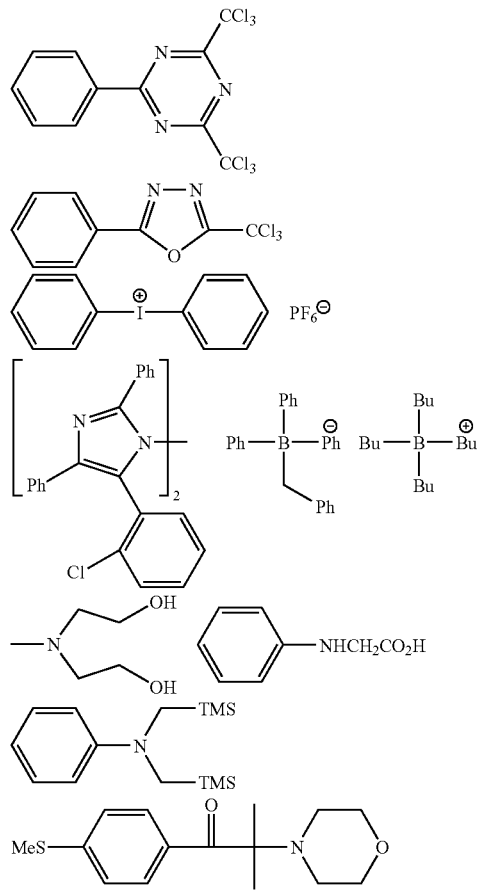

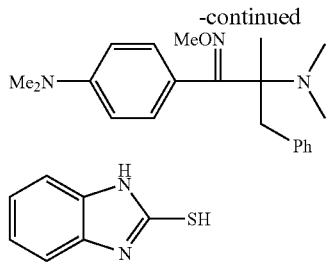

Similarly to the above-described sensitizing dye, these co-sensitizers can be subjected to various chemical modifications for the purpose of improving the properties of the photosensitive layer. Examples of the method which can be used therefor include binding to the sensitizing dye, activator, addition-polymerizable unsaturated compound or other parts, introduction of a hydrophilic moiety, introduction of a substituent for improving compatibility and inhibiting crystallization or for enhancing adhesion, and formation into a polymer.

These co-sensitizers can be used individually or in combination of two or more. The co-sensitizer is suitably used in an amount of 0.05 to 100 parts by mass, preferably from 1 to 80 parts by mass, more preferably from 3 to 50 parts by mass, per 100 parts by mass of the compound having an ethylenic unsaturated double bond.

(D2) Polymerization Inhibitor

In the present invention, in order to prevent unnecessary thermal polymerization of the polymerizable compound having an ethylenic unsaturated double bond during the production or storage of the photosensitive composition, a small amount of a thermal polymerization inhibitor is preferably added in addition to the above-described basic components. Suitable examples of the thermal polymerization inhibitor include hydroquinone, p-methoxyphenol, di-tert-butyl-p-cresol, pyrogallol, tert-butylcatechol, benzoquinone, 4,4'-thiobis(3-methyl-6-tert-butylphenol), 2,2'-methylenebis(4-methyl-6-tert-butylphenol) and N-nitrosophenylhydroxyamine cerous salt. The amount of the thermal polymerization inhibitor added is preferably from about 0.01 to about 5 mass % based on the mass of the entire composition. If desired, in order to prevent polymerization inhibition by oxygen, a higher fatty acid derivative such as behenic acid and behenic acid amide may be added and localized on the photosensitive layer surface during drying after the coating. The amount of the higher fatty acid derivative added is preferably from about 0.5 to about 10 mass % based on the entire composition.

(D3) Colorant, Etc.

A dye or a pigment may also be added for the purpose of coloring the photosensitive layer. By this addition, the printing plate can be enhanced in the so-called suitability for plate inspection, such as visibility after plate-making and adaptability to an image density analyzer. Many dyes cause reduction in the sensitivity of the photopolymerization-type photosensitive layer and therefore, a pigment is preferably used as the coloring agent. Specific examples thereof include pigments such as phthalocyanine-base pigment, azo-base pigment, carbon black and titanium oxide, and dyes such as Ethyl Violet, Crystal Violet, azo-base dye, anthraquinone-base dye and cyanine-base dye. The amount of the dye or pigment added is preferably from about 0.5 to about 5 mass % based on the entire composition.

(D4) Other Additives

Other known additives may also be added, such as inorganic filler for improving physical properties of the hardened film, plasticizer, and ink receptivity agent which can improve the inking property on the photosensitive layer surface.

Examples of the plasticizer include dioctyl phthalate, didodecyl phthalate, triethylene glycol dicaprylate, dimethyl glycol phthalate, tricresyl phosphate, dioctyl adipate, dibutyl sebacate and triacetylglycerol. When a binder is used, the plasticizer can be added in an amount of 10 mass % or less based on the total mass of the compound having an ethylenic unsaturated double bond and the binder.

Furthermore, a UV initiator, a heat crosslinking agent and the like can also be added for strengthening the effect of heating and exposure after development and thereby enhancing the film strength (press life) which is described later.

Other than these, an additive or an interlayer for improving the adhesion between the photosensitive layer and a support or increasing the removal by development of the unexposed photosensitive layer may be used. For example, when a compound having relatively strong interaction with the substrate, such as compound having diazonium structure or phosphone compound, is added or undercoated, the adhesive property is improved and the press life can be enhanced, whereas when a hydrophilic polymer such as polyacrylic acid or polysulfonic acid is added or undercoated, the developability of the non-image area is improved and the scumming resistance can be enhanced.

In coating the photopolymerizable composition of the present invention on a support, the composition is used after dissolving it in an organic solvent of various types. Examples of the solvent used here include acetone, methyl ethyl ketone, cyclohexane, ethyl acetate, ethylene dichloride, tetrahydrofuran, toluene, ethylene glycol monomethyl ether, ethylene glycol monoethyl ether, ethylene glycol dimethyl ether, propylene glycol monomethyl ether, propylene glycol monoethyl ether, acetylacetone, cyclohexanone, diacetone alcohol, ethylene glycol monomethyl ether acetate, ethylene glycol ethyl ether acetate, ethylene glycol monoisopropyl ether, ethylene glycol monobutyl ether acetate, 3-methoxypropanol, methoxymethoxyethanol, diethylene glycol monomethyl ether, diethylene glycol monoethyl ether, diethylene glycol dimethyl ether, diethylene glycol diethyl ether, propylene glycol monomethyl ether acetate, propylene glycol monoethyl ether acetate, 3-methoxypropyl acetate, N,N-dimethylformamide, dimethyl sulfoxide, γ-butyrolactone, methyl lactate and ethyl lactate. These solvents can be used individually or as a mixture. The concentration of solid contents in the coating solution is suitably from 2 to 50 mass %.

The amount of the photosensitive layer coated on a support affects mainly sensitivity and developing property of the photosensitive layer and strength and press life of the exposure film and therefore, an appropriate amount is preferably selected according to use. If the amount coated is too small, insufficient press life results, whereas if it is excessively large, the sensitivity decreases and this disadvantageously requires a long time for the exposure and also for the development processing. In the case of a lithographic printing plate for scanning exposure, which is a main object of the present invention, the amount coated is, in terms of the mass after drying, suitably from about 0.1 to about 10 g/m$^2$, preferably from 0.5 to 5 g/m$^2$.

E. Support

In order to obtain a lithographic printing plate which is one main object of the present invention, the above-described photosensitive layer is preferably provided on a support having a hydrophilic surface. As the hydrophilic support, conventionally known hydrophilic supports for use in a lithographic printing plate can be used without limitation. The support used is preferably a plate-like material having dimensional stability. Examples thereof include paper, paper laminated with plastic (e.g., polyethylene, polypropylene, polystyrene), metal plate (e.g., aluminum, zinc, copper), plastic film (e.g., cellulose diacetate, cellulose triacetate, cellulose propionate, cellulose butyrate, cellulose acetate butyrate, cellulose nitrate, polyethylene terephthalate, polyethylene, polystyrene, polypropylene, polycarbonate, polyvinyl acetal), and paper or plastic film laminated or vapor-deposited with the above-described metal. If desired, the surface of the support may be subjected to an appropriate known physical or chemical treatment for the purpose of imparting hydrophilic property or improving the strength.

Among these supports, preferred are paper, polyester film and aluminum plate. In particular, aluminum plate has good dimensional stability, is relatively inexpensive and can provide a surface having excellent hydrophilic property or strength, if desired, by a surface treatment and therefore, aluminum plate is more preferred. A composite sheet comprising a polyethylene terephthalate film having bonded thereon an aluminum sheet, described in JP-B-48-18327, is also preferred.

The aluminum plate is preferably a pure aluminum plate or an alloy plate mainly comprising aluminum and containing a hetero-element in a slight amount, and may also be a plastic film having laminated or vapor-deposited thereon aluminum. Examples of the hetero-element contained in the aluminum alloy include silicon, iron, manganese, copper, magnesium, chromium, zinc, bismuth, nickel and titanium. The hetero-element content in the alloy is at most 10 mass % or less. The aluminum particularly preferred in the present invention is pure aluminum, but a perfectly pure aluminum is difficult to produce in view of the refining technique and therefore, a trace of hetero-element may be contained. The composition of the aluminum plate for use in the present invention is not specified, and an aluminum plate of conventionally known and employed material can be appropriately used. The thickness of the aluminum plate for use in the present invention is approximately from about 0.1 to about 0.6 mm, preferably from 0.15 to 0.4 mm, more preferably from 0.2 to 0.3 mm.

In the case of a support having a metal, particularly aluminum, surface, the support is preferably subjected to a surface treatment such as surface roughening (graining), soaking in an aqueous solution of sodium silicate, potassium fluorozirconate or phosphate, and anodization.

The surface roughening treatment of an aluminum plate is performed by various methods, for example, a method of mechanically roughening the surface, a method of electrochemically dissolving and roughening the surface, and a method of selectively and chemically dissolving the surface. For the mechanical surface roughening, known methods such as ball polishing, brush polishing, blast polishing and buff polishing can be used. The electrochemical surface roughening method includes a method of performing the treatment in an electrolytic solution such as hydrochloric acid or nitric acid, by applying an alternating current or direct current. A method of using both currents in combination disclosed in JP-A-54-63902 may also be used. If desired, in order to remove rolling oil from the surface, a degreasing treatment with a surfactant, an organic solvent or an alkaline aqueous solution is performed in advance of the surface roughening of the aluminum plate.

Furthermore, an aluminum plate subjected to surface roughening and then to soaking in an aqueous sodium silicate solution can be suitably used. As described in JP-B-47-5125, an aluminum plate subjected to anodization and then to soaking in an aqueous solution of alkali metal silicate is preferably used. The anodization treatment is performed by applying a current while using the aluminum plate as anode in an electrolytic solution comprising a single aqueous or non-aqueous solution of an inorganic acid such as phosphoric acid, chromic acid, sulfuric acid or boric acid, an organic acid such as oxalic acid or sulfamic acid, or a salt thereof, or comprising a combination of two or more of these solutions.

A silicate electrodeposition method described in U.S. Pat. No. 3,658,662 is also effective.

Furthermore, a surface treatment where a support subjected to electrolytic graining disclosed in JP-B-46-27481, JP-A-52-58602 and JP-A-52-30503 is combined with the above-described anodization treatment and sodium silicate treatment is also useful.

A support subjected to mechanical surface roughening, chemical etching, electrolytic graining, anodization treatment and sodium silicate treatment in this order disclosed in JP-A-56-28893 is also suitably used.

A support which is, after these treatments, undercoated, for example, with a water-soluble resin such as polyvinyl phosphonate, a polymer or copolymer having a sulfonate group on the side chain, a polyacrylic acid, a water-soluble metal salt (e.g., zinc borate), a yellow dye or an amine salt is also suitably used.

In addition, a sol-gel treated substrate obtained by covalent bonding of a functional group capable of causing an addition reaction under the action of a radical, disclosed in JP-A-7-154983, is also suitably used.

Other suitable examples include a support obtained by providing a water-resistant hydrophilic layer as a surface layer on an arbitrary support. Examples of the surface layer include a layer comprising an inorganic pigment and a binder described in U.S. Pat. No. 3,055,295 and JP-A-56-13168, a hydrophilic swelling layer described in JP-A-9-80744, and a sol-gel film comprising titanium oxide, polyvinyl alcohol and a silicic acid described in JP-T-8-507727 (the term "JP-T" as used herein means a "published Japanese translation of PCT patent application").

These hydrophilization treatments are performed not only to render the support surface hydrophilic but also to prevent a harmful reaction of the photopolymerizable composition provided on the support and at the same time, improve the adhesive property and the like of the photosensitive layer.

F. Protective Layer

A lithographic printing plate for scanning exposure, which is a preferred embodiment of the present invention, is generally exposed in air. Therefore, a protective layer is preferably further provided on the photopolymerizable composition layer. The protective layer prevents the photosensitive layer from invasion of a low molecular compound which inhibits the image formation reaction generated by exposure in the photosensitive layer, such as oxygen present in air and basic substance, and enables exposure in air. In this meaning, the property required of the protective layer is low permeability to a low molecular compound such as oxygen. Furthermore, the protective layer preferably has a property of not substantially inhibiting the transmission of light used for exposure, exhibiting excellent adhesive property to the photosensitive layer and being easily removable in the development step after exposure. Techniques regarding such a protective layer have been heretofore proposed and these are described in detail in U.S. Pat. No. 3,458,311 and JP-A-55-49729. The material which can be used for the protective layer is preferably, for example, a water-soluble polymer compound having relatively excellent crystallinity, and specific known examples thereof include water-soluble polymers such as polyvinyl alcohol, polyvinylpyrrolidone, acidic celluloses, gelatin, gum arabic and polyacrylic acid. Among these, a polyvinyl alcohol is preferably used as the main component, because most excellent results are given on the basic properties such as oxygen blocking ability and removal by development.

The polyvinyl alcohol for use in the protective layer may be partially substituted by an ester, an ether or an acetal as long as it contains an unsubstituted vinyl alcohol unit for ensuring necessary oxygen blocking ability and water solubility. Also, other copolymerization component may be present in a part of the polyvinyl alcohol. Examples of the polyvinyl alcohol include those having a hydrolysis degree of 71 to 100 mol% and a weight average molecular weight of 300 to 2,400. Specific examples thereof include PVA-105, PVA-110, PVA-117, PVA-117H, PVA-120, PVA-124, PVA-124H, PVA-CS, PVA-CST, PVA-HC, PVA-203, PVA-204, PVA-205, PVA-210, PVA-217, PVA-220, PVA-224, PVA-217EE, PVA-217E, PVA-220E, PVA-224E, PVA-405, PVA-420, PVA-613 and L-8 produced by Kuraray Co., Ltd.

The component (selection of PVA and use of additives), coating amount and the like of the protective layer are selected by taking account of oxygen blocking ability, removal by development, fogging, adhesion and scratch resistance. In general, the oxygen blocking ability is higher as the hydrolysis ratio of PVA is higher (as the content of unsubstituted vinyl alcohol unit in the protective layer is higher) and as the layer thickness is larger, and this is advantageous in view of sensitivity. However, if the oxygen blocking ability is increased to an extreme degree, a problem arises, for example, an unnecessary polymerization reaction takes place during production or stock storage, or undesirable fogging or thickening of image line is caused at the image exposure. The adhesion to the image area and scratch resistance are also very important factors in view of handling of the plate. That is, when a hydrophilic layer comprising a water-soluble polymer is laminated on a lipophilic polymerization layer, layer separation readily occurs due to poor adhesive strength and the separated portion brings about problems such as hardening failure due to polymerization inhibition by oxygen. For improving the adhesion between these two layers, various techniques have been proposed. For example, U.S. Pat. Nos. 292,501 and 44,563 describe a technique where from 20 to 60 mass % of an acrylic emulsion or a water-insoluble vinylpyrrolidone-vinyl acetate copolymer is mixed in a hydrophilic polymer mainly comprising polyvinyl alcohol and the polymer is laminated on a polymerization layer, whereby sufficiently high adhesive property can be obtained. These known techniques all can be applied to the protective layer of the present invention. The coating method of this protective layer is described in detail, for example, in U.S. Pat. No. 3,458,311 and JP-A-55-49729.

The protective layer may also be imparted with other functions. For example, when a colorant (e.g., water-soluble dye) having excellent transmitting property of light from 350 to 450 nm used for exposure and capability of efficiently absorbing light of 500 nm or more is added, the safe light aptitude can be more enhanced without decreasing the sensitivity.

G. Image Formation Method and Plate-Making Process

In the case where a photosensitive material using the photopolymerizable composition of the present invention is used as an image forming material, an image is usually obtained by performing image exposure and then removing the unexposed area of the photosensitive layer by a developer. At the time of using the above-described photopolymerizable composition for the preparation of a lithographic printing plate, examples of the developer which can be preferably used include developers described in JP-B-57-7427. Particularly, an aqueous solution of an inorganic alkali agent such as sodium silicate, potassium silicate, sodium hydroxide, potassium hydroxide, lithium hydroxide, sodium tertiary phosphate, sodium secondary phosphate, ammonium tertiary phosphate, ammonium secondary phosphate, sodium metasilicate, sodium bicarbonate and aqueous ammonia, or an organic alkali agent such as monoethanolamine and diethanolamine, is suitably used. The alkali agent is added to give an alkali solution having a concentration of 0.1 to 10 mass %, preferably from 0.5 to 5 mass %.

If desired, the alkaline aqueous solution may contain a small amount of a surfactant or an organic solvent such as benzyl alcohol, 2-phenoxyethanol and 2-butoxyethanol. Examples thereof include those described in U.S. Pat. Nos. 3,375,171 and 3,615,480.

Also, developers described in JP-A-50-26601, JP-A-58-54341, JP-B-56-39464 and JP-B-56-42860 are also excellent.

A particularly preferred developer is a developer described in JP-A-2002-202616, which contains a nonionic compound represented by the following formula (IV) and has a pH of 11.5 to 12.8 and an electric conductivity of 3 to 30 mS/cm:

A—W                                                                      (IV)

wherein A represents a hydrophobic organic group with the logP of A—H being 1.5 or more, and W represents a nonionic hydrophilic organic group with the logP of W—H being less than 1.0.

This developer component is described in detail in paragraphs (0024) to (0067) of JP-A-2002-202616.

In the present invention, the nonionic compound represented by formula (IV) is effectively added to have a concentration of 0.1 to 15 mass %, preferably from 1.0 to 8.0 mass %, in the developer.

In the plate-making process of the lithographic printing plate precursor of the present invention, if desired, the entire surface may be heated before or during exposure or between exposure and development. By this heating, the image forming reaction in the photosensitive layer is accelerated and this provides advantageous effects such as enhancement of sensitivity or press life and stabilization of sensitivity. Also, after-heating or exposure of the entire surface of the image after development is effective for the purpose of improving the image strength and press life. Usually, the heating before development is preferably performed under a mild condition of 150° C. or less. When the heating temperature is 150° C. or less, the problem of fogging does not occur in the non-image area. For the heating after development, a very strong condition is employed. This heating is usually performed at 200 to 500° C. When the heating temperature is 200° C. or more, a satisfactory image-strengthening activity can be obtained, and when the temperature is 500° C. or less, a problem such as deterioration of the support or thermal decomposition of the image area does not arise.

In exposing the lithographic printing plate for scanning exposure of the present invention, known methods can be used without limitation. The wavelength of the light source is preferably from 350 to 450 nm and, specifically, an InGaN-base semiconductor laser is suitable. The exposure mechanism may be any of an internal drum system, an external drum system and a flat bed system. In the present invention, the photosensitive layer components can be made soluble in neutral water or weakly alkali solution by using components having high water solubility and in the case of a lithographic printing plate having such a construction, a system of loading the plate on a press and performing exposure-development on the press can also be employed.

As the available laser light source of 350 to 450 nm, the followings can be used:

as a gas laser, an Ar ion laser (364 nm, 351 nm, 10 mW to 1 W), a Kr ion laser (356 nm, 351 nm, 10 mW to 1 W) and a He—Cd laser (441 nm, 325 nm, 1 mW to 100 mW), as a solid laser, a combination of Nd:YAG(YVO$_4$) and SHG crystal×2 times (355 nm, 5 mW to 1 W), and a combination of Cr:LiSAF and SHG crystal (430 nm, 10 mW), as a semiconductor laser system, a KNbO$_3$ ring resonator (430 nm, 30 mW), a combination of a wave guide-type wavelength conversion element and an AlGaAs or InGaAs semiconductor (380 to 450 nm, 5 to 100 mW), a combination of a wave guide-type wavelength conversion element and an AlGaInP or AlGaAs semiconductor (300 to 350 nm, 5 to 100 mW), and AlGaInN (350 to 450 nm, 5 to 30 mW), and as a pulse laser, a N$_2$ laser (337 nm, pulse: 0.1 to 10 mJ) and XeF (351 nm, pulse: 10 to 250 mJ).

Among these, an AlGaInN semiconductor laser (commercially available InGaN-base semiconductor laser, 400 to 410 nm, 5 to 30 mW) is preferred in view of wavelength properties and cost.

The apparatus employing a scanning exposure system for exposing the lithographic printing plate includes, as the exposure mechanism, an internal drum system, an external drum system and a flat bed system and for the light source, the above-described light sources excluding the pulse laser all can be used. In practice, the following exposure devices are particularly preferred in view of relationship between the sensitivity of photo-sensitive material and the plate-making time:

a single beam exposure device employing an internal drum system and using one gas or solid laser light source;

a multi-beam exposure device employing a flat bed system and using a large number of semiconductor lasers (10 or more); and a multi-beam exposure device employing an external drum system and using a large number of semiconductor lasers (10 or more)

In the above-described laser direct drawing-type lithographic printing plate, the following equation (eq. 1) is generally established among sensitivity X (J/cm$^2$) of photosensitive material, exposure area S (cm$^2$) of photo-sensitive material, power q (W) of one laser light source, number n of lasers and entire exposure time t (s):

$$X \cdot S = n \cdot q \cdot t \qquad \text{(eq. 1)}$$

i) In the Case of Internal Drum (Single Beam) System

The following equation (eq. 2) is generally established among laser rotation number f (radian/s), sub-scanning length Lx (cm) of photosensitive material, resolution Z (dot/cm) and entire exposure time t (s):

$$f \cdot Z \cdot t = Lx \qquad \text{(eq. 2)}$$

ii) In the Case of External Drum (Multi-Beam) System

The following equation (eq. 3) is generally established among drum rotation number F (radian/s), sub-scanning length Lx (cm) of photosensitive material, resolution Z (dot/cm), entire exposure time t (s) and number (n) of beams:

$$F \cdot Z \cdot n \cdot t = Lx \qquad \text{(eq. 3)}$$

iii) In the Case of Flat Bed (Multi-Beam) System

The following equation (eq. 4) is generally established among rotation number H (radian/s) of polygon mirror, sub-scanning length Lx (cm) of photosensitive material, resolution Z (dot/cm), entire exposure time t (s) and number of beams (n):

$$H \cdot Z \cdot n \cdot t = Lx \qquad \text{(eq. 4)}$$

When resolution (2,560 dpi) required of a practical printing plate, plate size (A1/B1, sub-scanning length: 42 inch), exposure condition of about 20 sheets/1 hour and photosensitive properties (photosensitive wavelength, sensitivity: about 0.1 mJ/cm$^2$) of the photosensitive composition of the present invention are substituted for the equations above, it can be understood that a combination of the photosensitive material of the present invention with a multi-beam exposure system of a semiconductor laser is more preferred. Furthermore, by taking account also of operation, cost and the like, a combination with a semiconductor laser multi-beam exposure device employing an external drum system is most preferred.

Other examples of the exposure light which can be used for the photopolymerizable composition of the present invention include an ultra-high pressure, high-pressure, medium-pressure or low-pressure mercury lamp, a chemical lamp, a carbon arc lamp, a xenon lamp, a metal halide lamp, various visible or ultraviolet laser lamps, a fluorescent lamp, a tungsten lamp and sunlight. As for use, the photopolymerizable composition of the present invention can be widely applied to those known as uses of a photo-curing resin without limitation, in addition to the application to a lithographic printing plate for scanning exposure. For example, when the photopolymerizable composition is applied to a liquid photopolymerizable composition used, if desired, in combination with a cation-polymerizable compound, a highly sensitive stereolithographic material can be obtained. Also, a hologram material can be obtained by utilizing change in the refractive index accompanying the photopolymerization. The photopolymerizable composition can also be applied to various transfer materials (e.g., separation photosensitive material, toner development sensitive material) by utilizing change in the surface adhesive property accompanying the photopolymerization. In addition, the photopolymerizable composition can be applied to photo-curing of microcapsules, production of electronic material such as photoresist, or photocurable resin material such as ink, coating material and adhesive.

EXAMPLES

The present invention is described below by referring to Examples, however, the present invention is not limited to these Examples.

Synthesis Example 1

Synthesis of (D1):

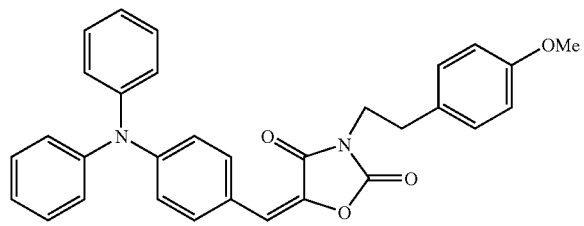

(D1)

Diphenylbenzaldehyde (4.1 g), 0.6 g of pyrrolidine and 3.5 g of 3-[2-(4-methoxyphenyl)ethyl]-1,3-oxazolidine-2,4-dione were dissolved in 50 ml of methanol and then stirred under reflux for 2 hours. After the completion of reaction, the solution was allowed to cool to room temperature, as a result, a yellow crystal was precipitated. The precipitated crystal was filtered, added to 100 ml of methanol and stirred for 1 hour. Thereafter, the crystal was filtered and dried to obtain 6.7 g of Compound (D1) (yield: 91%, purity: 99.3%).

The identification was performed by $^1$H-NMR (CDCl$_3$), infrared absorption spectrum, mass spectrometry spectrum and elemental analysis. Melting point (149–152° C.), electron absorption spectrum (THF): absorption maximum wavelength: 397 nm, absorption maximum molar absorptivity: 37,100, oxidation potential (CH$_3$CN, vs Ag/AgCl): +1.01 V.

Examples 1 to 14 and Comparative Examples 1 to 5

(Preparation of Support)

A 0.3 mm-thick aluminum plate was etched by soaking it in 10 mass % sodium hydroxide at 60° C. for 25 seconds, washed with running water, neutralized and washed with 20 mass % nitric acid and then washed with water. This plate was subjected to an electrolytic surface roughening treatment in an aqueous 1 mass % nitric acid solution by using a sinusoidal alternating wave form current with an anode time electricity of 300 coulomb/dm$^2$. Subsequently, the plate was soaked in an aqueous 1 mass % sodium hydroxide solution at 40° C. for 5 seconds, then soaked in an aqueous 30 mass % sulfuric acid solution to perform the desmutting at 60° C. for 40 seconds, and thereafter anodized for 2 minutes in an aqueous 20 mass % sulfuric acid solution at a current density of 2 A/dm$^2$ to give an anodic oxide film thickness of 2.7 g/m$^2$. The surface roughness was measured and found to be 0.3 µm (Ra indication according to JIS B0601).

On the back surface of the thus-treated substrate, the following sol-gel reaction solution was coated by a bar coater and dried at 100° C. for 1 minute, thereby preparing a support having provided thereon a backcoat layer in a dry coated amount of 70 mg/M$^2$.

Sol-Gel Reaction Solution:

| Tetraethyl silicate | 50 parts by mass |
|---|---|
| Water | 20 parts by mass |
| Methanol | 15 parts by mass |
| Phosphoric acid | 0.05 parts by mass |

When these components were mixed and stirred, generation of heat started in about 5 minutes. After allowing the reaction to proceed for 60 minutes, a solution shown below was added to prepare a coating solution for backcoat layer.

| Pyrogallol formaldehyde condensation resin (molecular weight: 2,000) | 4 parts by mass |
|---|---|
| Dimethyl phthalate | 5 parts by mass |
| Fluorine-containing surfactant (N-butylperfluorooctane sulfonamide ethylacrylate/poly-oxyethylene acrylate copolymer, molecular weight: 20,000) | 0.7 parts by mass |
| Methanol silica sol (produced by Nissan Chemical Industries, methanol: 30 mass %) | 50 parts by mass |
| Methanol | 800 parts by mass |

(Preparation of Photosensitive Layer)

On the thus-treated aluminum plate, a photo-polymerizable composition having a composition shown below was coated to a dry coated amount of 1.0 to 2.0 g/m$^2$ and dried at 80° C. for 2 minutes to form a photosensitive layer.

| Pentaerythritol tetraacrylate | 1.6 g |
|---|---|
| Allyl methacrylate/methacrylic acid/N-isopropyl acrylamide copolymer | 1.9 g |

-continued

| | |
|---|---|
| (copolymerization molar ratio: 70/15/15) | |

Photopolymerization initiation system (shown in Table 1)

| | |
|---|---|
| Sensitizing dye (D1, D9, D12, D14, D20, D24, D28, D29, D32, DR-1 to DR-3) | X g |
| Activator (A-1 to A-6) | Y g |
| Co-sensitizer (C-1 to C-3) | Z g |
| Fluorine-containing nonionic surfactant (Megafac F-780F, produced by Dai-Nippon Ink & Chemicals, Inc.) | 0.03 g |
| Thermal polymerization inhibitor (N-nitrosophenylhydroxylamine aluminum salt) | 0.01 g |
| Pigment dispersion | 2.0 g |

Composition of pigment dispersion:

| | |
|---|---|
| Composition: Pigment Blue 15:6 | 15 parts by mass |
| Allyl methacrylate/methacrylic acid copolymer (copolymerization molar ratio: 83/17) | 10 parts by mass |
| Cyclohexanone | 15 parts by mass |
| Methoxypropyl acetate | 20 parts by mass |
| Propylene glycol monomethyl ether | 40 parts by mass |
| Methyl ethyl ketone | 20 g |
| Propylene glycol monomethyl ether | 20 g |

(Preparation of Protective Layer)

On the photosensitive layer, an aqueous solution containing 3 mass % of polyvinyl alcohol (saponification degree: 98 mol%, polymerization degree: 550) was coated to a dry coated mass of 2 g/m² and dried at 100° C. for 2 minutes.

(Evaluation of Sensitivity)

On the thus-obtained photosensitive material, Fuji Step Guide (a gray scale where the transmission optical density discontinuously changes at $\Delta D=0.15$) manufactured by Fuji Photo Film Co., Ltd. was tightly contacted. Thereafter, exposure was performed to give a known exposure energy by using a xenon lamp through an optical filter and then development was performed by soaking the material in a developer having a composition shown below at 25° C. for 10 seconds. The highest step number when the image was completely removed was read, the exposure energy amount at that time was determined, and the sensitivity (unit: mJ/cm²) was calculated. As the energy amount is smaller, the sensitivity is higher. For the purpose of estimating the exposure aptitude for a short-wave semiconductor laser, exposure was performed with a monochromic light of 400 nm by using Kenko BP-40 as the optical filter. The results are shown in Table 1. Furthermore, the photosensitive material before exposure was stored under enforced storage conditions of a humidity of 50% and 70° C. for 3 days and then, the presence or absence of crystal precipitation on the photosensitive material was confirmed with an eye. A sample having no crystal precipitation was rated ○, and a sample having crystal precipitation was rated x. The results are shown together in Table 1.

(Composition of Developer)

An aqueous solution with a pH of 12.0 having the following composition.

| | |
|---|---|
| Potassium hydroxide | 0.2 g |
| 1K Potassium Silicate (SiO₂/K₂O = 1.9) | 2.4 g |
| Compound of formula 1 below | 5.0 g |
| Tetrasodium ethylenediaminetetraacetate | 0.1 g |
| Water | 91.3 g |

TABLE 1

(formula 1)

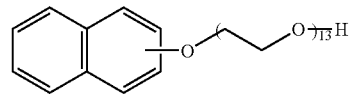

| | Initiation System | | | | | |
|---|---|---|---|---|---|---|
| | Sensitizing Dye (X g) | Activator (Y g) | Co-Sensitizer (Z g) | Coated Amount (mg/m²) | Clear Sensitivity (mJ/cm²) | Crystal Precipitation |
| Example 1 | D1 (0.10) | A-1 (0.12) | none | 1.1 | 0.25 | ○ |
| Example 2 | D1 (0.10) | A-2 (0.15) | C-2 (0.20) | 1.1 | 0.15 | ○ |
| Example 3 | D1 (0.10) | A-3 (0.10) | none | 1.1 | 0.30 | ○ |
| Example 4 | D1 (0.10) | A-4 (0.12) | C-3 (0.20) | 1.1 | 0.25 | ○ |
| Example 5 | D1 (0.10) | A-5 (0.12) | C-1 (0.20) | 1.1 | 0.35 | ○ |
| Example 6 | D1 (0.10) | A-6 (0.12) | none | 1.1 | 0.40 | ○ |
| Example 7 | D29 (0.08) | A-2 (0.10) | C-1 (0.15) | 1.3 | 0.15 | ○ |
| Example 8 | D9 (0.12) | A-4 (0.12) | C-3 (0.15) | 1.2 | 0.30 | ○ |
| Example 9 | D24 (0.12) | A-1 (0.15) | none | 1.4 | 0.30 | ○ |
| Example 10 | D32 (0.08) | A-2 (0.15) | C-2 (0.10) | 1.4 | 0.15 | ○ |
| Example 11 | D12 (0.10) | A-2 (0.12) | none | 1.1 | 0.25 | ○ |
| Example 12 | D28 (0.10) | A-5 (0.12) | none | 1.4 | 0.30 | ○ |
| Example 13 | D20 (0.12) | A-1 (0.12) | C-2 (0.15) | 1.2 | 0.25 | ○ |
| Example 14 | D14 (0.10) | A-2 (0.15) | none | 1.1 | 0.20 | ○ |
| Comparative Example 1 | D1 (0.15) | none | none | 1.1 | Image was not formed. | — |
| Comparative Example 2 | none | A-2 (0.12) | none | 1.1 | 1.5 | — |
| Comparative Example 3 | DR-1 (0.08) | A-2 (0.15) | none | 1.1 | 0.15 | X |

TABLE 1-continued (formula 1)

Naphthyl−O−(CH$_2$CH$_2$O)$_{13}$−H

| | Initiation System | | | | |
|---|---|---|---|---|---|
| | Sensitizing Dye (X g) | Activator (Y g) | Co-Sensitizer (Z g) | Coated Amount (mg/m$^2$) | Clear Sensitivity (mJ/cm$^2$) | Crystal Precipitation |
| Comparative Example 4 | DR-2 (0.08) | A-2 (0.12) | none | 1.1 | 0.30 | X |
| Comparative Example 5 | DR-3 (0.08) | A-2 (0.10) | C-2 (0.25) | 1.1 | 1.5 | ○ |

As is apparent from Table 1, in Examples 1 to 14 using the initiation system of the present invention, practically satisfied high sensitivity is exhibited. Comparison with Comparative Examples 1 to 5 not using the initiation system of the present invention reveals that the initiation system of the present invention can express high sensitivity by virtue of the combination use of sensitizing dye and activator. Furthermore, it is seen from Examples 1 to 6 that activators of the present invention over a wide range can be applied irrespective of the sensitization mechanism. In addition, comparison between Example 2 and Comparative Example 3 and between Example 8 and Comparative Example 4 suggests that the structural feature contributing to the effect of preventing crystal precipitation is in the partial structure of the sensitizing dye of the present invention, and this is an unexpected discovery.

Examples 15 to 21 and Comparative Example 6

Lithographic printing plates were prepared by the following procedure and evaluated on the printing performance. The results are shown in Table 2.

[Pretreatment of Support]

The surface of a 0.3 mm-thick aluminum plate formed of a material 1S was grained by using a No. 8 nylon brush and a water suspension of 800-mesh pumice stone, and then thoroughly washed with water. The resulting aluminum plate was etched by soaking it in 10 mass % sodium hydroxide at 70° C. for 60 seconds, washed with running water, neutralized and washed with 20 mass % nitric acid and then washed with water. This plate was subjected to an electrolytic surface roughening treatment in an aqueous 1 mass % nitric acid solution by using a sinusoidal alternating wave form current with an anodic time electricity of 300 coulomb/dm$^2$. The surface roughness was measured and found to be 0.45 μm (Ra indication according to JIS B0601).

[Hydrophilization of Support Surface]

The support treated above was soaked in an aqueous solution containing 2.5 mass % of No. 3 sodium silicate (SiO$_2$=28 to 30%, Na$_2$O=9 to 10%, Fe=0.02% or less), at a pH of 11.2 and 70° C. for 13 seconds, and then washed with water. The amount of Si element was determined by X-ray fluorescence analysis of the surface and from the obtained value, the amount of silicate on the surface was determined to be 10 mg/m$^2$.

[Coating of Interlayer]

A coating solution having a composition (A) shown below was prepared and coated on the surface of the hydrophilized support by using a whirler under the condition of 180 rpm such that the amount of phenyl-phosphonic acid coated became 20 mg/m$^2$, and then dried at 80° C. for 30 seconds.

(Coating Solution A for Interlayer)

| Phenyl phosphonate | 0.07 to 1.4 g |
|---|---|
| Methanol | 200 g |

[Coating of Photosensitive Layer]

A photosensitive solution having a composition shown below was prepared, coated on the support having provided thereon the interlayer, by using a whirler to have a coated amount of 1.0 to 2.0 g/m$^2$, and then dried at 100° C. for 1 minute.

(Photosensitive Solution)

| Addition-polymerizable compound (compound shown in Table 2) | 1.8 g |
|---|---|
| Binder polymer (compound shown in Table 2) | 2.0 g |
| Sensitizing dye (compound shown in Table 2) | 0.15 g |
| Activator (compound shown in Table 2) | 0.1 g |
| Co-sensitizer (compound shown in Table 2) | 0.2 g |
| Coloring pigment dispersion | 2.0 g |

Composition of pigment dispersion:

| Pigment Blue 15:6 | 15 parts by mass |
|---|---|
| Allyl methacrylate/methacrylic acid copolymer (copolymerization molar ratio: 83/17) | 10 parts by mass |
| Cyclohexanone | 15 parts by mass |
| Methoxypropyl acetate | 20 parts by mass |
| Propylene glycol monomethyl ether | 40 parts by mass |
| Thermal polymerization inhibitor (N-nitrosophenylhydroxylamine aluminum salt) | 0.01 g |
| Surfactant (Megafac F-177, produced by Dai-Nippon Ink & Chemicals, Inc.) | 0.02 g |
| Methyl ethyl ketone | 20.0 g |
| Propylene glycol monomethyl ether | 20.0 g |

[Coating of Protective Layer]

On this photosensitive layer, an aqueous solution containing 3 mass % of polyvinyl alcohol (saponification degree: 98 mol %, polymerization degree: 550) was coated to have a dry coated mass of 2 g/m² and dried at 100° C. for 2 minutes.

[Exposure of Lithographic Printing Plate Precursor]

The thus-obtained lithographic printing plate precursor was subjected to solid image exposure and dot image exposure of 175 lines/inch and from 1 to 99% dots in steps of 1%, by using monochromatic light of 400 nm as a light source and adjusting the exposure power to give an exposure energy density of 200 µJ/cm² on the plate surface.

[Development/Plate-Making]

A predetermined developer (shown in Table 2) and Finisher FP-2W produced by Fuji Photo Film Co., Ltd. were charged into an automatic developing machine LP-850 manufactured by Fuji Photo Film Co., Ltd. and the development/plate-making of the exposed plate was performed at a developer temperature of 30° C. for a development time of 18 seconds to obtain a lithographic printing plate.

[Press Life Test]

The press used was R201 manufactured by Roland Co. and the ink used was GEOS-G (N) produced by Dai-Nippon Ink & Chemicals, Inc. The solid image area of the printed matter was observed and the press life was examined by the number of sheets when the image started thinning. As the number is larger, the press life is better.

[Dot Press Life Enforced Test]

The press used was R201 manufactured by Roland Co. and the ink used was GEOS-G (N) produced by Dai-Nippon Ink & Chemicals, Inc. When the 5,000th sheet from the initiation of printing was printed, the ink on the plate surface was cleaned by wiping the dotted part with a printing sponge impregnated with PS Plate Cleaner CL-2 produced by Fuji Photo Film Co., Ltd. Thereafter, 10,000 sheets were printed and the presence or absence of plate wearing of dots on the printed matter was observed with an eye.

[Scumming Test]

The press used was R 201 manufactured by Roland Co. and the ink used was GEOS-G (S) produced by Dai-Nippon Ink & Chemicals, Inc. The scumming was evaluated by observing the non-image area (unexposed area) of the printed matter.

(Addition-Polymerizable Compounds in Table 2)

(M-1)

Pentaerythritol tetraacrylate (NK Ester A-TMMT, produced by Shin-Nakamura Chemical Co., Ltd.)

(M-2)

Glycerin dimethacrylate hexamethylene diisocyanate urethane prepolymer (UA101H, produced by Kyoei-sha Chemical Co., Ltd.)

(Binder Polymers in Table 2)

(B-1)

Allyl methacrylate/methacrylic acid/N-isopropylacrylamide (copolymerization molar ratio: 67/13/20)

Acid value measured by NaOH titration: 1.15 meq/g

Weight average molecular weight measured by GPC: 130,000

(B-2)

Allyl methacrylate/methacrylic acid copolymer (copolymerization molar ratio: 83/17)

Acid value measured by NaOH titration: 1.55 meq/g

Weight average molecular weight measured by GPC: 125,000

(B-3)

Polyurethane resin as a condensation polymerization product of the following diisocyanates and diols.

4,4'-Diphenylmethane diisocyanate (MDI)

Hexamethylene diisocyanate (HMDI)

Polypropylene glycol, weight average molecular weight: 1,000 (PPG 1000)

2,2-Bis(hydroxymethyl)propionic acid (DMPA)/tetra-ethylene glycol (TEG)

Copolymerization molar ratio (MDI/HMDI/PPG 1000/DMPA/TEG): 40/10/11/26/13

Acid value measured by KOH titration: 50.5 meq/g

Weight average molecular weight measured by GPC: 65,000

(Developers in Table 2)

(DV-1)

An aqueous solution with a pH of 10 having the following composition.

| | |
|---|---|
| Monoethanolamine | 0.1 part by mass |
| Triethanolamine | 1.5 parts by mass |
| Compound of formula 2 below | 4.0 parts by mass |
| Compound of formula 3 below | 2.5 parts by mass |
| Compound of formula 4 below | 0.2 parts by mass |
| Water | 91.7 parts by mass |

(DV-2)

An aqueous solution with a pH of 10 having the following composition.

| | |
|---|---|
| Sodium hydrogencarbonate | 1.2 parts by mass |
| Sodium carbonate | 0.8 parts by mass |
| Compound of formula 2 below | 3.0 parts by mass |
| Compound of formula 3 below | 2.0 parts by mass |
| Compound of formula 4 below | 0.2 parts by mass |
| Water | 92.8 parts by mass |

(DV-3)

An aqueous solution with a pH of 13 having the following composition.

| | |
|---|---|
| 1K Potassium Silicate | 3.0 parts by mass |
| Potassium hydroxide | 1.5 parts by mass |
| Compound of formula 4 below | 0.2 parts by mass |
| Water | 95.3 parts by mass |

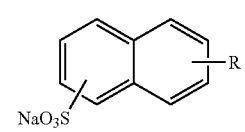

(formula 2)

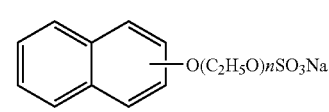

(formula 3)

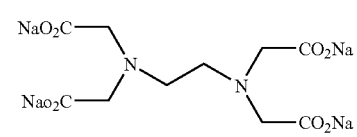

(formula 4)

(wherein R is H or $C_4H_9$ and n is about 4 (average))

(DV-4)

An aqueous solution with a pH of 12.0 having the following composition.

| | |
|---|---|
| Potassium hydroxide | 0.2 g |
| 1K Potassium Silicate (SiO$_2$/K$_2$O = 1.9) | 2.4 g |
| Compound of formula 1 above | 5.0 g |
| Tetrasodium ethylenediaminetetraacetate | 0.1 g |
| Water | 91.3 g |

TABLE 2

| | Photosensitive Layer | | | | | | Printing Performance | | |
|---|---|---|---|---|---|---|---|---|---|
| No. | Addition-Polymerizable Compound | Binder Polymer | Sensitizing Dye | Activator | Co-Sensitizer | Coated Amount (mg/m$^2$) | Composition of Developer | Press Life of Image Area | Press Life of Dot Area | Scumming of Non-Image Area |
| Example 15 | M-1 | B-1 | D25 | A-2 | C-1 | 1.4 | DV-4 | 78000 | good | good |
| Example 16 | M-1 | B-2 | D27 | A-2 | C-2 | 1.4 | DV-4 | 55000 | good | good |
| Example 17 | M-2 | B-3 | D5 | A-1 | C-2 | 1.2 | DV-4 | 95000 | good | good |
| Example 18 | M-1 | B-1 | D3 | A-3 | C-1 | 1.5 | DV-2 | 70000 | good | good |
| Example 19 | M-1 | B-1 | D31 | A-2 | C-3 | 1.4 | DV-1 | 75000 | good | good |
| Example 20 | M-2 | B-3 | D7 | A-2 | C-2 | 1.4 | DV-4 | 85000 | good | good |
| Example 21 | M-2 | B-3 | D22 | A-4 | C-3 | 1.4 | DV-3 | 65000 | good | good |
| Comparative Example 6 | M-1 | B-1 | none | A-1 | H-2 | 1.4 | DV-4 | flow of image | flow of image | good |

As is apparent from Table 2, the lithographic printing plate of the present invention provides an excellent lithographic printing plate by scanning exposure with high productivity under the condition capable of plate-making, namely under the exposure condition of very low energy. On the other hand, in Comparative Example 7 not using the initiation system of the present invention, a practically usable lithographic printing plate was not obtained.

Example 22

A lithographic printing plate precursor was prepared in the same manner as in Examples 1 to 14 except that the initiation system was changed to have a composition shown below and the thickness of the photopolymerization layer was changed to 1.5 g/m$^2$.

| | | |
|---|---|---|
| Initiation system | D22 | 0.10 g |
| | A-1 | 0.15 g |
| Co-sensitizer | C-2 | 0.2 g |

The obtained lithographic printing plate precursor was subjected to scanning exposure by using monochromatic light of 400 nm under the conditions of giving an exposure energy density of 0.25 mJ/cm$^2$. Thereafter, the plate was heated at 100° C. for 10 seconds and then subjected to the above-described development treatment.

A lithographic printing plate having a blue image with excellent visibility was obtained. When offset printing was performed by using the obtained plate and using a press KOR-D manufactured by Heidelberg, 50,000 sheets or more of a printed matter having excellent image density and scumming resistance could be obtained.

Example 23

The plate of Example 22 was exposed to yellow light for 1 hour before exposure and then plate-making and printing were performed thoroughly in the same manner as in Example 22. Good results completely the same as in Example 22 were obtained.

Example 24

The plate of Example 22 was stored for 3 days under enforced storage conditions of a humidity of 65% and 45° C. and then plate-making and printing were performed in the same manner as in Example 22. Good results the same as in Example 22 were obtained.

Example 25

A photosensitive layer comprising a composition shown below was coated on a PET film to have a coated amount of 2.0 g/m$^2$.

(Content in All Solid Contents of Photosensitive Layer)

| | |
|---|---|
| Binder resin (polymethyl methacrylate) | 90.5 wt % |
| Sensitizing dye (Compound D10) | 2.0 wt % |
| Activator A-6 | 5.5 wt % |
| Acid-achromatic dye (naphthalenesulfonate of Victoria Pure Blue) | 2.0 wt % |

The obtained blue-sensitive material was exposed for 30 seconds by using a metal halide lamp. The blue color completely disappeared and the material was changed to a pale yellow transparent film. This reveals that the initiation system of this Example functions also as an acid generator.

Example 26

The same operation as in Example 25 was performed except for changing the activator to A-7. Disappearance of color of the dye by light was observed similarly to Example 25.

Example 27

The same operation as in Example 26 was performed except for changing the activator to A-8. Disappearance of color of the dye by light was observed.

Structures of the compounds used in Examples and Comparative Examples, except for sensitizing dyes of the present invention and compounds of formulae 1 to 4, are shown below.

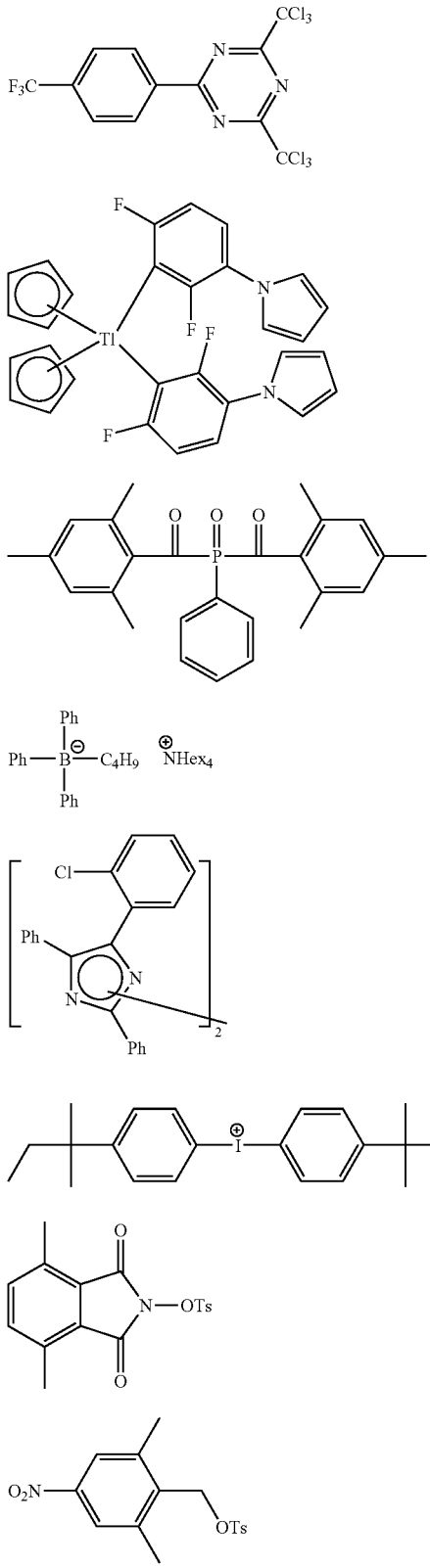

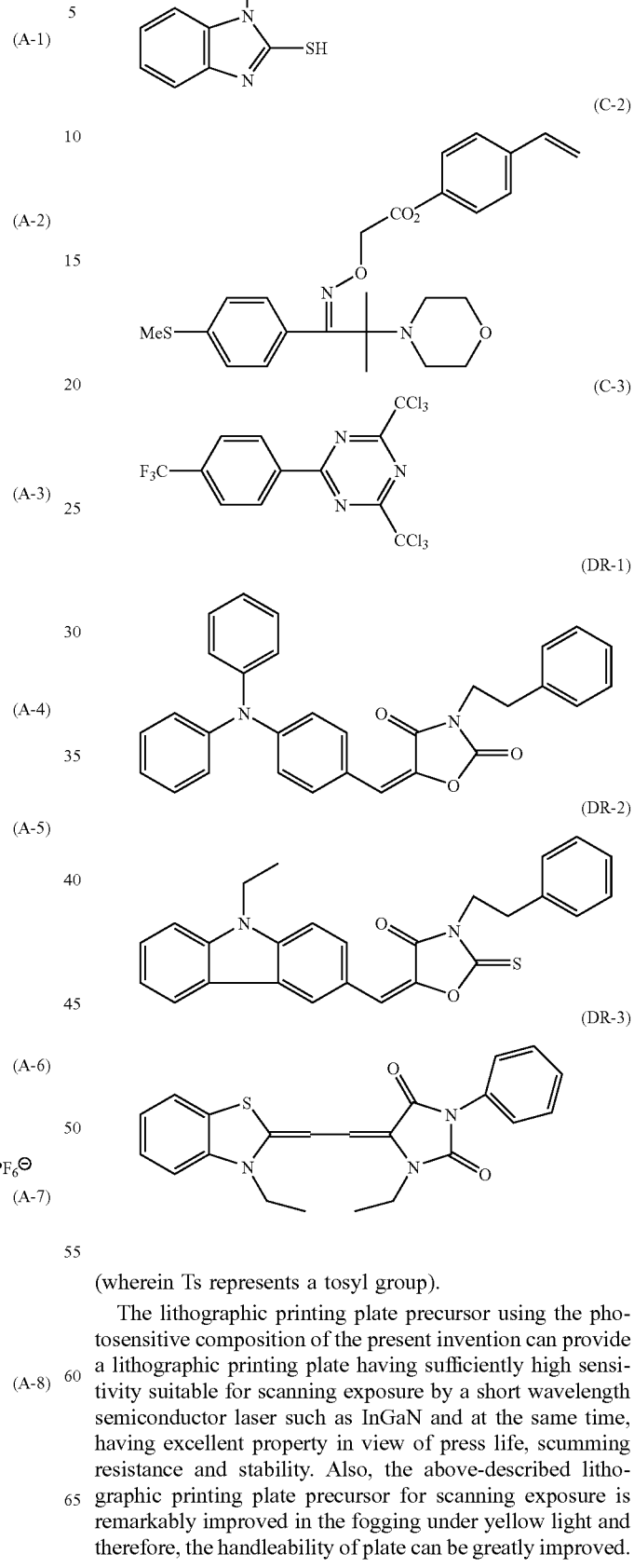

(wherein Ts represents a tosyl group).

The lithographic printing plate precursor using the photosensitive composition of the present invention can provide a lithographic printing plate having sufficiently high sensitivity suitable for scanning exposure by a short wavelength semiconductor laser such as InGaN and at the same time, having excellent property in view of press life, scumming resistance and stability. Also, the above-described lithographic printing plate precursor for scanning exposure is remarkably improved in the fogging under yellow light and therefore, the handleability of plate can be greatly improved.

Furthermore, the photo-initiation system of the present invention has excellent sensitivity and can generate a radical or an acid.

The entire disclosure of each and every foreign patent application from which the benefit of foreign priority has been claimed in the present application is incorporated herein by reference, as if fully set forth.

What is claimed is:

1. A compound represented by formula (1):

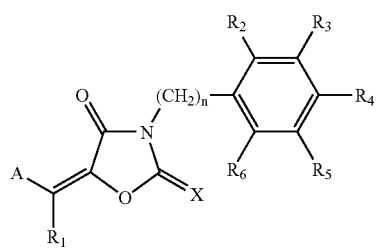

(1)

wherein A represents an aromatic or heterocyclic ring which may have a substituent; X represents an oxygen atom, a sulfur atom or $=NR_7$; $R_1$, $R_2$, $R_3$, $R_4$, $R_5$, $R_6$ and $R_7$ each independently represents a hydrogen atom or a monovalent nonmetallic atom group, provided that at least one of $R_2$, $R_3$, $R_4$, $R_5$ and $R_6$ is a substituent represented by $-OR_8$, in which $R_8$ independently represents a monovalent nonmetallic atom group; and n represents an integer of 1 to 6.

2. The compound according to claim 1, which is represented by formula (2):

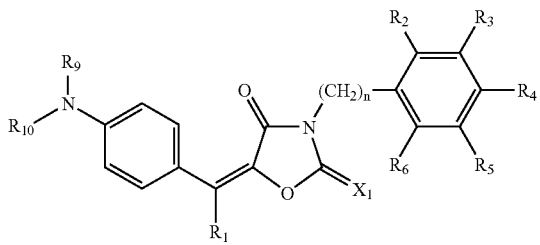

(2)

wherein $X_1$ represents an oxygen atom or a sulfur atom; $R_1$, $R_2$, $R_3$, $R_4$, $R_5$ and $R_6$ each independently represents a hydrogen atom or a monovalent nonmetallic atom group, $R_9$ and $R_{10}$ each independently represents a monovalent nonmetallic atom group, provided that at least one of $R_2$, $R_3$, $R_4$, $R_5$ and $R_6$ is a substituent represented by $-OR_8$, in which $R_8$ independently represents a monovalent nonmetallic atom group; and n represents an integer of 1 to 6.

3. A photosensitive composition comprising:
   (i) a sensitizing dye according to claim 1;
   (ii) an activator compound generating at least one of a radical and an acid by interacting the activator compound with light absorption of the sensitizing dye represented by formula (1) to cause chemical change; and
   (iii) a compound changing its physical or chemical property irreversibly by a reaction with at least one of the radical and the acid.

4. The photosensitive composition according to claim 3, wherein the sensitizing dye (i) is represented by formula (2):

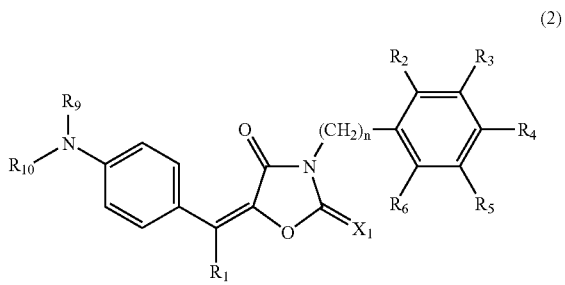

(2)

wherein $X_1$ represents an oxygen atom or a sulfur atom; $R_1$, $R_2$, $R_3$, $R_4$, $R_5$ and $R_6$ each independently represents a hydrogen atom or a monovalent nonmetallic atom group, $R_9$ and $R_{10}$ each independently represents a monovalent nonmetallic atom group, provided that at least one of $R_2$, $R_3$, $R_4$, $R_5$ and $R_6$ is a substituent represented by $-OR_8$, in which $R_8$ independently represents a monovalent nonmetallic atom group; and n represents an integer of 1 to 6.

5. The photosensitive composition according to claim 3, wherein the compound (iii) is an addition-polymerizable compound having an ethylenic unsaturated double bond.

6. The photosensitive composition according to claim 4, wherein the compound (iii) is an addition-polymerizable compound having an ethylenic unsaturated double bond.

7. A lithographic printing plate precursor comprising:
   a photosensitive layer including the photosensitive composition according to claim 3.

8. A method of forming image comprising:
   exposing a predetermined area of a photosensitive layer including the photosensitive composition according to claim 3.

9. The method according to claim 8, further comprising:
   developing one of the predetermined area and the other area.

* * * * *